United States Patent
Silberg et al.

(10) Patent No.: US 9,956,388 B2
(45) Date of Patent: May 1, 2018

(54) SYSTEMS AND METHODS FOR THERAPEUTIC AGENT DELIVERY

(71) Applicant: Sonescence, Inc., Santa Rosa, CA (US)

(72) Inventors: Barry Neil Silberg, Santa Rosa, CA (US); Seth Putterman, Malibu, CA (US)

(73) Assignee: Sonescence, Inc., Santa Rosa, CA (US)

(*) Notice: Subject to any disclaimer, the term of this patent is extended or adjusted under 35 U.S.C. 154(b) by 181 days.

(21) Appl. No.: 14/730,752

(22) Filed: Jun. 4, 2015

(65) Prior Publication Data
US 2016/0015953 A1 Jan. 21, 2016

Related U.S. Application Data

(60) Provisional application No. 62/007,709, filed on Jun. 4, 2014.

(51) Int. Cl.
*A61M 37/00* (2006.01)

(52) U.S. Cl.
CPC . *A61M 37/0092* (2013.01); *A61M 2205/3375* (2013.01)

(58) Field of Classification Search
CPC .................................. A61B 8/12; A61N 7/02
See application file for complete search history.

(56) References Cited

U.S. PATENT DOCUMENTS

| | | |
|---|---|---|
| 4,190,495 A | 2/1980 | Curtis, III |
| 4,368,203 A | 1/1983 | Okamura et al. |
| 4,982,730 A | 1/1991 | Lewis, Jr. |
| 5,016,615 A | 5/1991 | Driller et al. |
| 5,197,946 A | 3/1993 | Tachibana |
| 5,399,723 A | 3/1995 | Iinuma et al. |
| 5,559,108 A | 9/1996 | Kim et al. |
| 5,578,572 A | 11/1996 | Horwitz et al. |
| 5,580,575 A | 12/1996 | Unger et al. |
| 5,656,016 A | 8/1997 | Ogden |
| 5,884,631 A | 3/1999 | Silberg |
| 5,980,512 A | 11/1999 | Silberg |
| 6,018,678 A | 1/2000 | Mitagotri et al. |
| 6,030,374 A | 2/2000 | McDaniel |
| 6,039,048 A | 3/2000 | Silberg |

(Continued)

FOREIGN PATENT DOCUMENTS

| | | |
|---|---|---|
| RU | 2119769 C1 | 10/1998 |
| RU | 2175565 C2 | 10/2001 |

(Continued)

OTHER PUBLICATIONS

Barua et al,. "Convection-Enhanced Drug Delivery to the Brain: Therapeutic Potential and Neuropathological Considerations," Brain Pathology (2014) 24:117-127.

(Continued)

*Primary Examiner* — Hien Nguyen
(74) *Attorney, Agent, or Firm* — Kilpatrick, Townsend & Stockton LLP

(57) ABSTRACT

According to some embodiments herein, systems for delivering therapeutic agents and/or methods of using such systems are provided. The systems can be configured to administer solution comprising therapeutic agent to a subject, and can further comprise an ultrasound applicator for applying ultrasound energy to the subject.

6 Claims, 7 Drawing Sheets

(56) References Cited

U.S. PATENT DOCUMENTS

| | | |
|---|---|---|
| 6,041,253 A | 3/2000 | Kost et al. |
| 6,074,657 A | 6/2000 | Brown |
| 6,403,056 B1 | 6/2002 | Unger |
| 6,428,491 B1 | 8/2002 | Weiss |
| 6,484,052 B1 | 11/2002 | Visuri |
| 6,565,521 B1 | 5/2003 | Silberg |
| 6,569,099 B1 | 5/2003 | Babaev |
| 6,623,444 B2 | 9/2003 | Babaev |
| 7,025,735 B2 | 4/2006 | Soring |
| 7,083,572 B2 | 8/2006 | Unger et al. |
| 7,326,235 B2 | 2/2008 | Edwards |
| 7,981,442 B2 | 7/2011 | Hood et al. |
| 8,050,752 B2 | 11/2011 | Babaev |
| 8,747,384 B2 | 6/2014 | Silberg |
| 2002/0099356 A1 | 7/2002 | Unger et al. |
| 2003/0044354 A1 | 3/2003 | Carpenter, Jr. et al. |
| 2003/0092667 A1 | 5/2003 | Tachibana et al. |
| 2004/0162546 A1 | 8/2004 | Liang et al. |
| 2004/0236268 A1 | 11/2004 | Mitragotri et al. |
| 2007/0167619 A1 | 7/2007 | Love et al. |
| 2007/0232962 A1 | 10/2007 | Zumeris et al. |
| 2008/0009764 A1 | 1/2008 | Davies |
| 2008/0154157 A1 | 6/2008 | Altshuler et al. |
| 2008/0319375 A1 | 12/2008 | Hardy |
| 2011/0040235 A1 | 2/2011 | Castel |
| 2011/0301528 A1 | 12/2011 | Silberg |
| 2011/0314914 A1 | 12/2011 | Gregg et al. |
| 2012/0041309 A1 | 2/2012 | Coussios et al. |
| 2012/0128776 A1 | 5/2012 | Chlon et al. |
| 2012/0259222 A1 | 10/2012 | Coussios et al. |
| 2012/0271169 A1 | 10/2012 | Coussios et al. |
| 2013/0006153 A1 | 1/2013 | Lewis |
| 2013/0041311 A1 | 2/2013 | Kohane et al. |
| 2013/0175226 A1 | 7/2013 | Coussios et al. |
| 2013/0251222 A1* | 9/2013 | Huang .................. A61B 8/13 382/131 |
| 2013/0281916 A1 | 10/2013 | Wagstaffe et al. |
| 2014/0144237 A1* | 5/2014 | Komatsu .............. G01N 29/022 73/579 |
| 2014/0200505 A1 | 7/2014 | Molinari et al. |
| 2014/0276367 A1 | 9/2014 | Kersten et al. |
| 2014/0288483 A1 | 9/2014 | Silberg |
| 2014/0308654 A1 | 10/2014 | Kay et al. |
| 2014/0377849 A1 | 12/2014 | Kay et al. |
| 2015/0004677 A1 | 1/2015 | Kay et al. |
| 2015/0343079 A1* | 12/2015 | Kim .................... A61K 9/127 424/9.51 |

FOREIGN PATENT DOCUMENTS

| | | |
|---|---|---|
| RU | 2218886 C2 | 12/2003 |
| RU | 2320381 C2 | 3/2008 |
| WO | 2015/059460 A1 | 4/2015 |
| WO | 2015/075442 A2 | 5/2015 |

OTHER PUBLICATIONS

Bratzler, Dale W., et al., "Use of Antimicrobial Prophylaxis for Major Surgery: Baseline Results From the National Surgical Infection Prevention Project", Arch Surg., (Feb. 2005), vol. 140, pp. 174-182.

Byl, Nancy, "The Use of Ultrasound as an Enhancer for Transcutaneous Drug Delivery: Phonophoresis", Pharmacology Series, Physical Therapy (Jun. 1995), vol. 75, No. 6, 15 pages.

Champoux, N. Et al., "Single-dose pharmacokinetics of ampicillin and tobramycin administered by hypodermoclysis in young and older healthy volunteers", Br J Clin Pharmacol, (1996), 42:325-331.

Dudley, Michael N., et al., "Comparative Penetration of Cefonicid and Cefazolin into the Atrial Appendage and Pericardial Fluid of Patients Undergoing Open-Heart Surgery", Antimicrobial Agents and Chemotherapy, (Sep. 1984), vol. 26, No. 3, p. 347-350.

Dyson, M. et al., "Stimulation of healing of varicose ulcers by ultrasound", Ultrasonics (Sep. 1976), pp. 232-236.

Forsberg et al., "Subharmonic imaging of contrast agents," *Ultrasonics*, (2000) 38:93-98.

Foulds, George, Joseph P. Stankewich, David C. Marshall, Mark M. OBrien, et al., Pharmacokinetics of Sulbactam in Humans, (May 1983), Antimicrobial Agents and Chemotherapy, vol. 25 No. 5, 692-699.

Frisoli, Jr., A. et al., "Subcutaneous Hydration by Hypodermoclysis: A Practical and Low Cost Treatment for Elderly Patients", Drugs & Aging, (Apr. 2000), 16 (4): 313-319.

Frohly et al., "Ultrasonic cavitation monitoring by acoustic noise power measurement," The Journal of the Acoustical Society of America, (2012) 108(5).

Hockham et al., "A Real-Time Controller for Sustaining Thermally Relevant Acoustic Cavitation During Ultrasound Therapy," IEEE Transactions on Ultrasonics, Ferroelectrics, and Frequency Control, (Dec. 2010) 57(12):2685-2694.

Hompland et al., "Interstitial Fluid Pressure and Associated Lymph Node Metastasis Revealed in Tumors by Dynamic Contrast-Enhanced MRI," *Cancer Research*, (2012) 72(19):4899-4908.

Kernodle, Douglas S. et al., "Association of Borderline Oxacillin-Susceptible Strains of *Staphylococcus aureus* with Surgical Wound Infections", Journal of Clinical Microbiology, (Jan. 1988), vol. 36, No. 1, pp. 219-222.

Lavery, Lawrence A., et al., "Validation of the Infectious Diseases Society of America's Diabetic Foot Infection Classification System", Clinical Infectious Diseases, (Jan. 17, 2007), 44:562-5.

Mangram, Alcicia J., et al., "Guideline for Prevention of Surgical Site Infection, 1999", Infection Control and Hospital Epidemiology, (Apr. 1999), vol. 20, No. 4, pp. 247-278.

Newman, M. K. et al., "Effects of Ultrasound Alonf and Combined with Hydrocortisone Injections by Needle or Hypospray", Presented as part of the Scientific pgrgram of the International Conference of Ultrasonics in Medicine, sponsored by the American Institute of Ultrasonics in Medicine, Los Angles, CA, (Sep. 6-7, 1957), pp. 206-209.

Ohge et al., "An Additional Dose of Cefazolin for Intraoperative Prophylaxis" Jpn J Surg (1999) 29:1233-1236.

Tranquart et al., "Clinical Use of Ultrasound Tissue Harmonic Imaging," Ultrasound in Med. & Biol., (1999) 25(6):889-894.

Tsukamoto, Akira, et al., "1-MHz ultrasound enhances internal diffusivity in agarose gels", Applied Acoustics (2013) 74:1117-1121.

Turos, Edward et al., "Penicillin-bound polyacrylate nanoparticles: Restoring the activity of β-lactam antibiotics against MRSA", Bioorganic & Medicinal Chemistry Letters, (Jun. 15, 2007) 17(2):3468-3472.

Wiggins, C.E., CL Nelson, R Clarke and CH Thompson, "Concentration of antibiotics in normal bone after intravenous injection", (1978), The Journal of Bone and Joint Surgery, 60, pp. 90-96.

As-filed U.S. Appl. No. 12/405,616, filed Mar. 17, 2009.
As-filed U.S. Appl. No. 13/205,097, filed Aug. 8, 2011.
As-filed U.S. Appl. No. 14/297,110, filed Jun. 5, 2014.
As-filed U.S. Appl. No. 14/725,694, filed May 29, 2015.
As-filed U.S. Appl. No. 14/738,606, filed Jun. 12, 2015.
As-filed U.S. Appl. No. 13/374,221, filed Dec. 15, 2011.
As-filed U.S. Appl. No. 14/725,734, filed May 29, 2015.
International Search Report dated Sep. 15, 2015, for PCT/US2015/034228 filed Jun. 4, 2015 (4 pgs.).

* cited by examiner

SYSTEMS AND METHODS FOR THERAPEUTIC AGENT DELIVERY

CROSS REFERENCE TO RELATED APPLICATIONS

The present application claims the benefit of U.S. Provisional Patent Application No. 62/007,709 filed Jun. 4, 2014, the disclosure of which is incorporated herein by reference in its entirety.

BACKGROUND

Embodiments herein generally relate to systems for therapeutic agent delivery and methods of using such systems.

Soft tissue infections are a major global health issue. About 325,000 new cases are diagnosed each year. When an inadequate concentration of antibiotic is used to treat a given infection, antibiotic resistant strains of bacteria develop that are increasingly difficult to treat. Patients with MRSA cellulitis of the lower extremity, especially those with impaired circulation, such as diabetics, are even more difficult to treat with standard delivery methods of antibiotics, such as oral or intravenous administration, because an adequate concentration of antibiotic cannot be delivered to the target tissues. Consequently over 10% of these cases end up in amputation and over $25 billion is spent annually on chronic wounds.

While recent developments in ultrasound driven drug delivery show promise against such infections and with other treatments (e.g., cancer, colonization, inflammation treatment, etc.), further improvements may be desired.

SUMMARY

In some aspects, a system for delivering a therapeutic agent to a target tissue in a subject is provided. The system can comprise a container configured to hold a fluid comprising the therapeutic agent. The system can comprise at least one of a vacuum source or an inert gas source in gas communication with the container, in which the vacuum source and inert gas source are configured to control a partial pressure of solubilized gas in the fluid. The system can comprise a pump in fluid communication with the container. The system can comprise a tissue interface in fluid communication with the pump, in which the pump is configured to control a flow of fluid from the container to the tissue interface. The system can comprise an ultrasound applicator configured to broadcast energy transcutaneously at a frequency from about 20 kHz to about 10 MHz and a power density from about 0.1 watts/cm$^2$ to about 10 watts/cm$^2$. The system can comprise a sensor (e.g., piezoelectric or the like) configured to detect an acoustic reaction of the subject upon broadcasting of the energy. In some embodiments, the system further comprises a processor in data communication with the sensor and the pump, in which the processor is configured to control the operation of the pump in response to data from the sensor. In some embodiments, the system further comprises a processor in data communication with the sensor and the ultrasound applicator, wherein the processor is configured to control operation of the ultrasound applicator in response to data from the sensor. In some embodiments, the processor is in data communication with the sensor, the pump, and the ultrasound applicator, so that the processor is configured to control operation of the pump and the ultrasound applicator in response to data from the sensor. In some embodiments, the pump comprises a peristaltic pump. In some embodiments, the container is configured to fluidly connect to a source of fluid comprising the therapeutic agent. In some embodiments, the system further comprises an ultrasound generator in communication with the ultrasound applicator. In some embodiments, the system further comprises a foot switch configured to control the operation of the ultrasound generator. In some embodiments, the subject is a human. In some embodiments, the subject is a non-human animal. In some embodiments, the ultrasound applicator is configured to broadcast energy at a frequency from about 20 kHz to about 5 MHz. In some embodiments, the ultrasound applicator is configured to broadcast energy at a power density from about 1 watts/cm$^2$ to about 5 watts/cm$^2$. In some embodiments, the system is configured to pulse the broadcast ultrasound energy. In some embodiments, a therapeutically effective concentration of therapeutic agent is delivered to the target tissue.

According to some aspects, a system for delivering a therapeutic agent to a target tissue in a subject is provided. The system can comprise a container configured to hold a fluid comprising the therapeutic agent. The system can comprise a cannula administering the fluid to a vicinity of the target tissue, wherein the cannula is in fluid communication with the container. The system can comprise an ultrasound applicator configured to broadcast energy transcutaneously at a frequency from about 20 kHz to about 10 MHz and a power density from about 0.1 watts/cm$^2$ to about 10 watts/cm$^2$. The system can comprise a computing unit for regulating an amount of induced cavitation in fluid after delivery of the fluid to the subject. In some embodiments, the system further comprises a sensor configured to detect an acoustic reaction of the subject upon broadcasting of the energy. In some embodiments, the system further comprises a processor in data communication with the sensor. In some embodiments, the computing unit may control an amount of cavitation of the fluid in response to data from the sensor. In some embodiments, the computing unit may control a pump in response to data from the sensor, thereby controlling the administration of fluid to the target tissue. In some embodiments, the sensor is configured to detect a broad band response and a harmonic response. In some embodiments, the processor is configured to perform a fast Fourier transform (FFT) on the detected acoustic reaction, thereby measuring a broad band response and harmonic response. In some embodiments, the computing unit controls at least one of the frequency or power of the broadcast energy, thereby regulating an amount of cavitation. In some embodiments, the computing unit controls a vacuum source in gas communication with the fluid. In some embodiments, the computing unit controls a source of inert gas in gas communication with the fluid. In some embodiments, the cannula comprises an infuser. In some embodiments, the cannula is coupled with a pump configured to control administration of the fluid to the subject. In some embodiments, the pump comprises a peristaltic pump. In some embodiments, the system further comprises a foot pedal configured to control the operation of the ultrasound applicator. In some embodiments, the container is configured to fluidly connect to a source of fluid comprising the therapeutic agent. In some embodiments, the subject is a human. In some embodiments, the subject is a non-human animal. In some embodiments, the ultrasound applicator is configured to broadcast energy at a frequency from about 20 kHz to about 5 MHz. In some embodiments, the ultrasound applicator is configured to broadcast energy at a power density from about 1 watts/cm$^2$ to about 5 watts/cm$^2$. In some embodiments, the system is configured to pulse the broadcast ultrasound energy. In some embodiments, a therapeutically effective concentration of therapeutic agent is delivered to the target tissue.

According to some aspects, a method of dispersing a therapeutic agent in a target tissue is provided. The method can comprise providing a system comprising a container configured to hold a fluid comprising the therapeutic agent, an ultrasound applicator configured to broadcast energy transcutaneously at a frequency from about 2 kHz to about 10 MHz and a power density from about 0.1 watts/cm$^2$ to about 10 watts/cm$^2$, and a tissue interface in fluid communication with the container. The method can comprise contacting an area at or near the target tissue in the subject with a tissue interface of the system, in which the subject is in need of dispersal of a therapeutic agent in a target tissue. The method can comprise administering a solution comprising the therapeutic agent to the subject via the tissue interface. The method can comprise applying ultrasound energy at or near the area. The method can comprise automatically adjusting at least one of (a) a frequency of the ultrasound energy; (b) a power of the ultrasound energy; or (c) a rate of administration of the solution comprising the therapeutic agent in response to acoustic feedback from application of the ultrasound energy. In some embodiments, the method further comprises pulsing of the ultrasound energy in response to acoustic feedback from application of the ultrasound energy. In some embodiments, the method further comprises providing a desired partial pressure of inert gas in the solution comprising therapeutic agent prior to administering the solution. In some embodiments, the ultrasound energy is applied transcutaneously. In some embodiments, the concentration delivered to the target tissue is therapeutically effective. In some embodiments, the concentration delivered to the target tissue would be toxic if delivered at the same concentration as when given systemically to the subject.

In some embodiments, systemic side effects of certain therapeutic agents can be avoided or prevented. For example, intravenous Vancomycin is the only route available to treat local tissue infection, which necessarily requires high dosages in order to obtain the desired local concentration. The high dosages, however, are often associated with severe systemic side effects. With delivery of Vancomycin directly to the target tissues by this method, extremely small total dosages can be used to achieve the desired therapeutic effect, thus avoiding the side effects. For example, when the usual dose, (one gram (1000 mg) of intravenous Vancomycin) is every twelve hours, a target tissue concentration of 10 μg/ml. is the goal. With this method, Vancomycin is injected into the target tissues at a concentration of 10 μg/ml so the infection can be treated with a total dose of as little as 0.1-0.3 mg of Vancomycin or 1/10,000 the systemic dose. In this embodiment, any therapeutic agent targeting a local infection or tumor that previously must be given intravenously can be given by this method.

In this embodiment, tissues with decreased blood supply such as lower limb infections in diabetics or radiated tissue after cancer treatment can be treated with local delivery of the therapeutic agent. For example, a patient with a chest wall recurrence of breast cancer in a radiated field typically cannot be given enough chemotherapy intravenously in order to treat the tumor. Using methods and systems disclosed herein, the chemotherapeutic agent can be delivered at a measured concentration directly to the tumor without systemic toxicity.

In some embodiments, a system for ultrasonic delivery of a therapeutic agent may be provided. The system may include an ultrasound transducer configured to deliver ultrasound energy toward an injected solution with the therapeutic agent dissolved therein to disperse the therapeutic agent into interstitial space of the target tissue. A sensor may be configured to monitor an acoustic response of the target tissue generated in response to ultrasound delivered by the ultrasound transducer. A controller (computing unit or the like) may be coupled with the sensor and the ultrasound transducer. The controller may be configured to monitor the dispersal of the injected solution with the therapeutic agent dissolved therein based on the acoustic response of the target tissue monitored by the sensor. The controller may be further configured to adjust the ultrasound delivery depending on the monitored acoustic response of the target tissue.

The sensor may be further configured to measure a baseline acoustic response from the target tissue. The controller may be configured to identify an end point for the ultrasound delivery by comparing the monitored acoustic response of the target tissue to the measured baseline acoustic response of the target tissue. The controller may identify the end point for the ultrasound delivery when the monitored acoustic response of the target tissue returns to within a predetermined threshold of the measured baseline acoustic response of the target tissue.

The controller may be further configured to adjust the ultrasound delivery by automatically ceasing delivery of the ultrasound by the ultrasound transducer when the controller identifies an end point for the ultrasound delivery. The controller may be further configured to output a user alert to signal adjustments to the ultrasound delivery. The user alert may be associated with an end point of the ultrasound delivery. The sensor may be configured to monitor a harmonic, subharmonic, and/or broad band response of the target tissue generated in response to the applied ultrasound. The sensor may be configured to monitor a harmonic, subharmonic, and/or broad band response of the injected solution generated in response to the applied ultrasound. The sensor may be configured to monitor a harmonic, subharmonic, and/or broad band response of an interaction between the injected solution and the target tissue generated in response to the applied ultrasound. The controller may be configured to apply a Fast Fourier Transform to the monitored acoustic response of the target tissue to the applied ultrasound. The ultrasound transducer may be configured to deliver ultrasound at an applied frequency and wherein the sensor is configured to monitor target tissue acoustic responses at frequencies other than the applied frequency. In some embodiments, the controller may be configured to apply a filter to block an input frequency.

The sensor may be configured to monitor a second harmonic response of the target tissue. The sensor may be configured to monitor an acoustic response of the injected solution generated in response to the applied ultrasound. A majority of the acoustic response of the injected solution may be due to a concentration of dissolved gas within the injected solution. In some embodiments, the controller may be configured to adjust the ultrasound delivery without using an acoustic response of injected gas filled drug carriers and without using an acoustic response of contrast agent that is made of gas filled capsules.

A user input may be provided. The user input may be configured to receive a user inputted volume of injected solution, a user inputted depth of target tissue, and/or a user inputted area of target tissue. A temperature sensor may be coupled with the ultrasound transducer to monitor a temperature of a face of the ultrasound transducer. The controller may be coupled with the temperature sensor and configured to prevent or cease ultrasound delivery when the temperature of the face of the ultrasound transducer exceeds a safety threshold. The controller may be further configured to output a temperature safety warning in a manner perceptible to the user.

In further aspects of the present invention, a method of monitoring a level of dispersal of a therapeutic agent into a target tissue may be provided. The method may include energizing an ultrasound transducer to deliver ultrasound energy toward a bolus of injected solution including the therapeutic agent dissolved therein to disperse the bolus of injected solution with the therapeutic agent into interstitial space of the target tissue. The dispersal may atomize the therapeutic in the target tissue. The dispersal of the bolus of injected solution with the therapeutic agent into the interstitial space of the target tissue may be monitored by monitoring an acoustic response of the target tissue or the injected solution to the applied ultrasound during the ultrasound application. The method may further include adjusting the ultrasound delivery based on the monitored acoustic response of the target tissue or the injected solution to the applied ultrasound.

The method may further include measuring a baseline acoustic response from the target tissue. The baseline acoustic response of the target tissue may be associated with the acoustic response of the target tissue prior to injection of the solution. An end point for the ultrasound delivery may be identified by comparing the monitored acoustic response of the target tissue to the measured baseline acoustic response of the target tissue. Optionally, the monitored acoustic response of the target tissue may be compared to the measured baseline acoustic response of the target tissue by determining when the monitored acoustic response of the target tissue returns to within a predetermined threshold of the measured baseline acoustic response of the target tissue. The acoustic response of the target tissue or the injected solution may be monitored by monitoring a harmonic, subharmonic, and/or broad band response of the target tissue or the injected solution to the applied ultrasound. The method may further include monitoring a harmonic, subharmonic, and/or broad band response of an interaction between the injected solution and the target tissue. A Fast Fourier Transform may be applied to the monitored acoustic response of the target tissue or the injected solution to the applied ultrasound. The ultrasound transducer may deliver ultrasound at an applied frequency and the acoustic response of the target tissue may be monitored by monitoring target tissue acoustic responses at frequencies other than the applied frequency. In some embodiments, a second harmonic response from the target tissue or the injected solution is monitored.

Optionally, an end point of the ultrasound delivery may be identified without using an acoustic response of injected gas filled drug carriers or an acoustic response of an injected contrast agent of gas filled capsules. In some embodiments, a temperature of a face of the ultrasound transducer may be monitored, and ultrasound delivery may be prevented or ceased/terminated when the temperature of the face of the ultrasound transducer exceeds a safety threshold and outputting a temperature safety warning in a manner perceptible to the user.

In further aspects, a system for ultrasonic delivery of a therapeutic agent may be provided. The system may include an ultrasound transducer configured to deliver ultrasound energy at an applied frequency toward an injected solution with the therapeutic agent and a concentration of gas dissolved therein to disperse the therapeutic agent into interstitial space of the target tissue. A sensor may be provided that is configured to monitor an acoustic response of the concentration of gas dissolved in the injected solution at frequencies other than the applied frequency—the acoustic response of the dissolved gas may be generated in response to ultrasound delivered by the ultrasound transducer. A controller may be coupled with the sensor and the ultrasound transducer. The controller may be configured to monitor the dispersal of the injected solution with the therapeutic agent dissolved therein based on the acoustic response of the gas dissolved in the injected solution monitored by the sensor. The controller may be further configured to adjust the ultrasound delivery depending on the monitored acoustic response of the gas dissolved in the injected solution.

In some embodiments, the sensor may be further configured to monitor an acoustic response of the target tissue generated in response to the applied ultrasound and an acoustic response of an interaction between the injected solution and the target tissue generated in response to the applied ultrasound. The controller may be configured to identify an end point for the ultrasound delivery depending on the monitored acoustic response of the gas dissolved in the injected solution, the acoustic response of the target tissue, and the acoustic response of the interaction between the injected solution and the target tissue. Optionally, the controller may be configured to identify the end point for the ultrasound delivery by comparing a baseline target tissue acoustic response with the monitored acoustic response of the gas dissolved in the injected solution, the acoustic response of the target tissue, and/or the acoustic response of the interaction between the injected solution and the target tissue. In some embodiments, the controller may be configured to automatically cease the application of ultrasound upon the identification of the end point for the ultrasound delivery.

DETAILED DESCRIPTION

Figure 1:
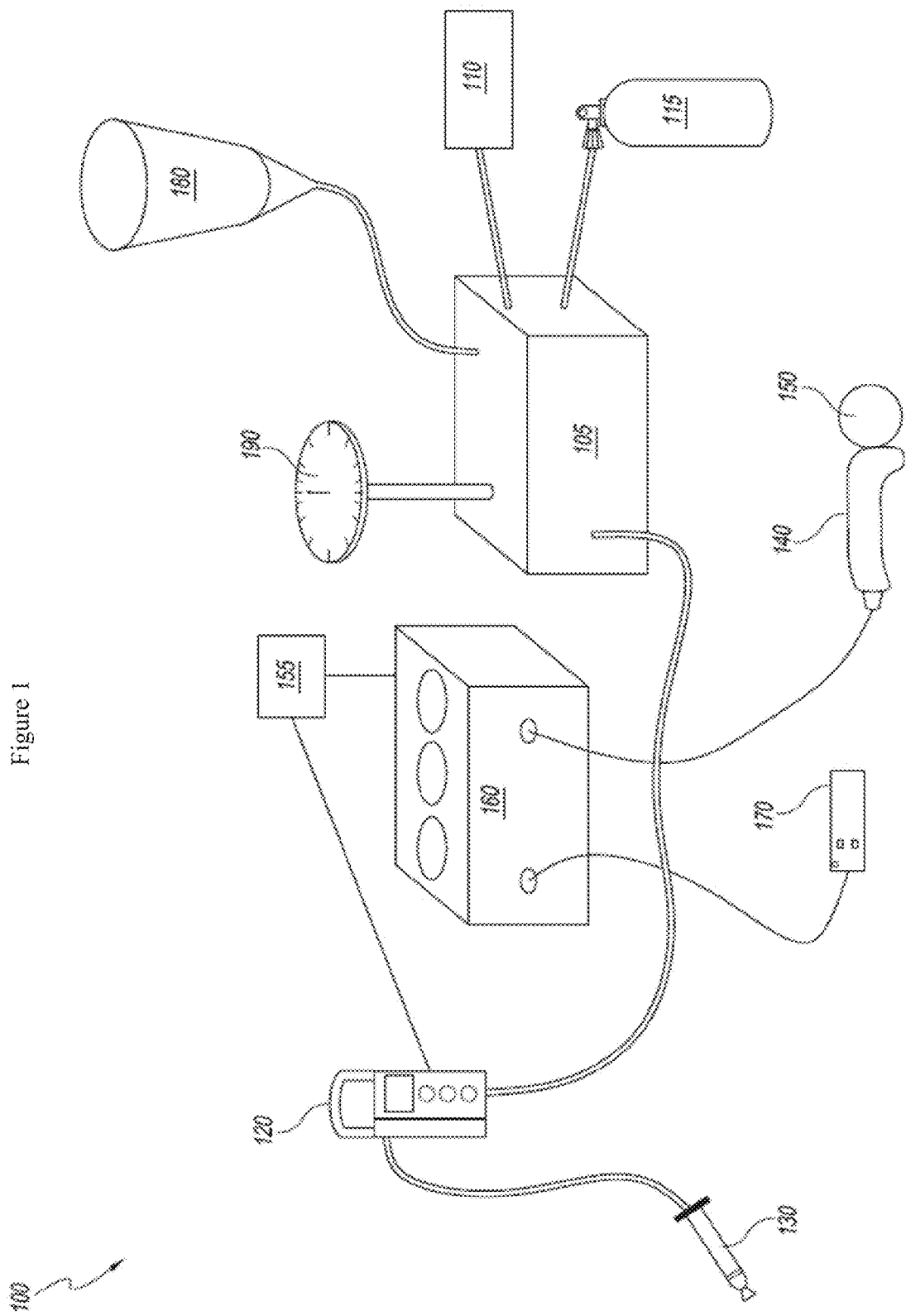
FIG. 1 is a schematic diagram illustrating a therapeutic agent delivery system in accordance with some embodiments herein.

According to some embodiments herein, therapeutic agent delivery systems and methods of using such systems are provided. In some subjects, a target tissue in need of a therapeutic agent can have limited access to blood supply. Systems and methods according to some embodiments herein can be configured for administering a solution comprising therapeutic agent to a subject and applying ultrasound energy during and/or after administration in order to efficiently disperse the therapeutic agent in the target tissue, even if the target tissue has low blood supply. Without being limited by any theory, it is contemplated that the dispersion of therapeutic agent can be a function of the amount of ultrasound energy-induced cavitation in solution or microstreaming of the solution. In some embodiments, the system regulates the partial pressure of gas in solution comprising the therapeutic agent, so as to achieve a desired amount and/or strength of cavitation upon administration. Accordingly, in some embodiments, a solution comprising therapeutic agent and a known partial pressure of inert gas is administered at or near a target tissue. In some embodiments, the system comprises a feedback sensor to dynamically control the administration of therapeutic agent and/or ultrasound energy in response to cavitation or microstreaming in the solution in the subject. Cavitation and/or microstreaming can be measured by detecting acoustic signals from the subject across a broad range of frequencies. As such, in some embodiments, the system and/or methods can deliver substantially higher concentrations of therapeutic agent at or near the target tissue than could be delivered through other routes, such as intravenous, oral, and the like. Moreover, systems and/or methods in conjunction with embodiments herein can deliver high concentrations of therapeutic agent directly to the target tissue, even if these concentrations would be toxic if administered through other routes, for example intravenously. By way of example, as the extremities of some diabetic patients can be characterized by low blood flow and can be subject to infection, systems and methods according to some embodiments herein can administer antibiotic agent at or near an infected tissue and apply ultrasound energy to disperse the antibiotic agent throughout the infected tissue. The methods and systems described herein may also be beneficial for treating various types of cancer (e.g., breast cancer, etc.) or other radiated tissue, venous ulcers, and chronic colonized wounds.

Systems

According to some embodiments herein, a system is provided for administration of therapeutic agent to a subject. The system can comprise a container configured to hold a fluid comprising the therapeutic agent, and an injection or infusion cannula for administering the fluid to a vicinity of the target tissue. The cannula can be in fluid communication with the container, and can comprise a tissue interface, and optionally a pump as described herein. The system can comprise an ultrasound applicator configured to broadcast energy to the administered fluid at a frequency from about 2 kHz to about 10 MHz and a power density from about 0.1 watts/cm$^2$ to about 10 watts/cm$^2$. In some embodiments, cavitation and/or microstreaming is induced in a fluid in the subject. In some embodiments, the system is configured to broadcast energy transcutaneously. The system can be configured to regulate an amount of cavitation and/or microstreaming induced in the fluid, for example by providing a desired partial pressure (or range of partial pressures) of inert gas in the solution comprising the therapeutic agent, and/or by dynamically adjusting at least one of ultrasound parameters or the rate of administering a solution comprising the therapeutic agent. In some embodiments, the system is configured to adjust ultrasound parameters and/or administration of solution comprising therapeutic agent in response to acoustic feedback from the subject. These embodiments and others are discussed in more detail herein.

FIG. 1 is a schematic diagram illustrating a system 100 according to some embodiments herein. The system 100 can comprise a container 105 configured to hold a fluid comprising therapeutic agent. The system 100 can further comprise a gas partial pressure controller for controlling a partial pressure of solubilized gas in the fluid. The gas partial pressure controller can comprise one or both of a vacuum 110 and inert gas source 115 in gas communication with solution in the container 105. The system 100 can further comprise a pump 120 in fluid communication with the container 105, and a tissue interface 130 in fluid communication with the pump 120, so that the pump 120 can direct solution from the container 105 to the tissue interface 130 for optional delivery to a subject. The system 100 can comprise an ultrasound applicator 140. In some embodiments, the ultrasound applicator 140 is configured to broadcast ultrasonic energy transcutaneously to a subject. Optionally, the system 100 can comprise a sensor 150 configured to detect an acoustic reaction of the subject upon broadcasting of the ultrasound energy. In some embodiments, the sensor 150 is directly attached to the ultrasound applicator 140. In some embodiments the sensor 150 is separate from the ultrasound applicator 140. The system 100 can comprise a processor 155 in data communication with the sensor 150. The system 100 can comprise an ultrasound generator 160 configured to provide ultrasound energy via the ultrasound applicator 140. Optionally, the system 100 can comprise a controller 170 for controlling the operation of the ultrasound generator 160 and/or ultrasound applicator 140. In some embodiments, the system 100 comprises a source of therapeutic agent 180 in fluid communication with the container 105. In some embodiments, the system 100 comprises a pressure gauge 190 configured to monitor pressure in the container 105. Optionally, the system 100 may include a temperature sensor for monitoring a temperature of a face of the ultrasound applicator 140. The temperature sensor may provide temperature feedback to the system 100 indicating when the face of the ultrasound applicator 140 is above a safety threshold. In response to the measured temperature exceeding the safety threshold, the system 100 may adjust ultrasound delivery (e.g., frequency or power), terminate the delivery of ultrasound and/or prevent the application of ultrasound and may also output a warning or alert to the user to avoid contacting a patient with the ultrasound applicator 170. The alert may be a visual, audio, and/or haptic alert. The alert may be generated at the ultrasound applicator 170 or by another portion of the system (e.g., ultrasound generator).

In some embodiments, the system comprises a single module, for example a module comprising the container 105, processor 155, pump 120, and ultrasound generator 160 with a handheld ultrasound applicator 140 attachment connected thereto. In some embodiments, the system comprises a container 105 in a first module, and the ultrasound generator 160 in a second module, with the processor 155 configured to control the pump 120 and also the ultrasound generator 160 and/or applicator 140.

Tissue Interfaces

A variety of tissue interfaces can be used in accordance with embodiments herein, for example cannulas (for example blunt-tipped infusion cannula), catheters, needles, and the like. A tissue interface can administer solution comprising therapeutic agent directly to a target tissue, or near a target tissue. In some embodiments, the tissue interface is configured for administration of the solution comprising therapeutic agent directly to the target tissue. In some embodiments, the tissue interface is configured for administration of the solution comprising therapeutic agent above the target tissue. In some embodiments, the tissue interface can be configured for administration of the solution comprising therapeutic agent to a periphery the target tissue. In some embodiments, the tissue interface can be configured for administration of the solution comprising therapeutic agent within 20 centimeters of the target tissue, for example within 20 centimeters, 19, 18, 17, 16, 15, 14, 13, 12, 11, 10, 9, 8, 7, 6, 5, 4, 3, 2, or 1 centimeters, including ranges between any two of the listed values.

The selection of an appropriate tissue interface can be performed by the skilled artisan, and can depend on a number of factors, for example type of therapeutic agent, quantity of solution to be delivered, type of subject, type of target tissue, and the like. In some embodiments, the tissue interface is configured for subcutaneous delivery of the therapeutic agent. In some embodiments, the tissue interface is configured for delivering the therapeutic agent to a body cavity, for example an abdominal cavity, intracranial space, or other body cavity. In some embodiments, a sterile tissue interface is provided.

Containers

A variety of containers can be used in accordance with embodiments herein. In some embodiments, the container is configured to hold a solution comprising therapeutic agent. In some embodiments, the container is rigid, for example a tank or tub. In some embodiments, the container is flexible, for example a bag or pouch. In some embodiments, the container is disposable, for example a single-use container. In some embodiments, the container is reusable. In some embodiments, a single container can be used for multiple administration cycles. In some embodiments, the container is detachable from the system, for example for cleaning and sterilization prior to and/or after an administration cycle.

For sanitary reasons, and also to minimize waste of therapeutic agents, it can be useful for the container to hold a single dose of therapeutic agent. The actual dose and volume can depend on a number of factors, for example the type of therapeutic agent, the desired concentration of the therapeutic agent, the disease or indication, characteristics of the subject, and the like. Accordingly, in some embodiments, the container is configured for holding any number of volumes of solution within a range, so that the partial pressure of inert gas can be regulated therein. In some embodiments the volume is about 1 cc to about 2000 cc or more, for example about 1 cc to about 1000 cc, about 1 cc to about 500 cc, about 1 cc to about 250 cc, about 10 cc to about 2000 cc, about 10 cc to about 1000 cc, about 10 cc to about 500 cc, about 10 cc to about 250 cc, about 100 cc to about 2000 cc, about 100 cc to about 1000 cc, about 100 cc to about 500 cc, or about 100 cc to about 250 cc. Exemplary total volumes of the container in accordance with some embodiments herein include, but are not limited to about 1 cc, 3, 5, 10, 15, 20, 25, 30, 35, 40, 45, 50, 60, 70, 80, 90, 100, 150, 200, 250, 300, 350, 400 450, 500, 550, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000 cc or more, including ranges between any two of the listed values.

The container can be in fluid communication with a source of therapeutic agent. In some embodiments, the container is connected directly to a source of therapeutic agent. In some embodiments, an intervening member, for example one or more of tubing, a valve, a filter, or an antechamber are positioned between the container and the source of therapeutic agent. In some embodiments, the valve is configured for manual control. In some embodiments, the valve is configured for automatic control, for example by a processor as described herein.

The container can be in fluid communication with a tissue interface. In some embodiments, the container is in fluid communication with a pump, which is in fluid communication with the tissue interface. In some embodiments, additional intervening members are positioned between the container and the tissue interface, for example tubing, pumps, valves, restrictions, heparin, and the like.

In some embodiments, the container is in gas communication with a gas partial pressure controller for increasing and/or decreasing the partial pressure of inert gas in the solution comprising therapeutic agent. Exemplary gas partial pressure controllers include a source of inert gas and/or a vacuum as described herein. In some embodiments, the container further comprises a solution mixer for mixing inert gas with solution to as to increase the partial pressure of inert gas in the solution. Exemplary solution mixers that can be used in accordance with some embodiments herein include stirrers (for example paddles, stir bars, and the like), magnetic beads, and agitators (for example rockers or shakers which can agitate the contents of the container by turning, rocking, or shaking all or part of the container). In some embodiments, the container is connected directly to a source of inert gas and/or vacuum. In some embodiments, an intervening member, for example one or more of tubing, a valve, or a filter are positioned between the container and the source of therapeutic agent. In some embodiments, the container is in gas communication with a meter such as a pressure gauge for monitoring the pressure or partial pressure of gas in solution. In some embodiments, gas valves are positioned in gas communication between the container and source or inert gas and/or vacuum for controlling the delivery of inert gas and/or application of vacuum. In some embodiments, the valve is configured for manual control. In some embodiments, the valve is configured for automatic control, for example by a processor, so that a particular set point or range of partial pressure of inert gas in the solution can be achieved.

Without being limited by any theory, the temperature of the solution comprising therapeutic agent can affect a number of factors, such as partial pressure of inert gas in solution, solubility of therapeutic agent in solution, or suitability for administration to a subject. Accordingly, in some embodiments, the container comprises a temperature controller for regulating the temperature of the solution in the container. In some embodiments a heater, for example one or more of a heating jacket, heating coil, hot plate, or burner, is provided for regulating the temperature of the container. In some embodiments, a cooling system, for example a cooling coil, radiative cooler, or source of coolant is provided for regulating the temperature of the container. In some embodiments the system is configured to maintain the solution at or below 37° C., for example at or below 37° C., 34° C., 30° C., 25° C., or 20° C. In some embodiments the system is configured to maintain the solution at or above 20° C., for example at or above 20° C., 25° C., 30° C., 34° C., or 37° C. In some embodiments, the system is configured to maintain the solution at about 5° C. or more, for example, 5° C., 10° C., 15° C., 20° C., 25° C., 26° C., 27° C., 28° C., 29° C., 30° C., 31° C., 32° C., 33° C., 34° C., 35° C., 36° C., 37° C., 38° C., 39° C., 40° C., 45° C., or 50° C., including ranges between any two of the listed values.

Therapeutic Agents

A variety of therapeutic agents can be provided in accordance with embodiments herein. Therapeutic agents useful in conjunction with some embodiments herein include, but are not limited to small molecules, organic compounds, proteins, peptides, antibodies, antibody fragments, vaccines, and the like. In some embodiments, the therapeutic agent is provided as a drug cocktail. As used herein "drug cocktail" refers to a combination of two or more therapeutically effective agents, for example two or more of any of the therapeutic agents described herein. In some embodiments, the drug cocktail comprises two, three, four, five, six, seven, eight, nine, ten, or more different therapeutic agents, including ranges between any two of the listed values. In some embodiments, a drug cocktail further includes additional ingredients, such as a pharmaceutically acceptable carrier or excipient, buffer, one or more sugars, and/or salts.

The therapeutic agent can be provided in appropriate form for delivery to a desired target tissue. By way of example, the systems and methods disclosed herein can be useful for distributing a solution comprising therapeutic agent in a variety of tissues with limited blood supply. Exemplary tissues include, but are not limited to soft tissues, skin, bone, tendons, muscles, joints, joint capsules, vessels, subcutaneous tissues such as subcutaneous fat, lungs, internal organs, abdominal cavities, abdominal cavity, other body cavities, intracranial space, tissue within the spinal column or cranium, neural tissue, or tumors.

Various cancers can have low access to blood supply, for example a chest wall recurrence of breast cancer in a radiated field with limited blood supply. Accordingly, in some embodiments, the tissue comprises cancerous cells, for example a tumor. As such, the therapeutic agent can comprise an anti-cancer agent for example a chemotherapy agent such as daunorubicin, doxorubicin, epirubicin, idarubicin, pirarubicin, aclarubicin, mitoxantrone, paclitaxel, docetaxel, podophyllotoxin, irinotecan, topotecan, actinomycin, bleomycin, plicamycin, and mitomycin, cyclophosphamide, methotrexate, pemetrexed, a deoxynucleoside analog (e.g. cytarabine, gemcitabine, decitabine, azacitidine, fludarabine, nelarabine, cladribine, clofarabine or pentostatin), a monoclonal antibody (e.g. an anti-EGFR antibody, an anti-her2 antibody, an anti-her3 antibody, or an anti-VEGF antibody), and the like, including combinations of any of the listed items.

Optionally, the target tissue may comprise brain tissue or cancerous brain tissue. In some embodiments, a drug may be directly delivered to the brain tissue for treating a cancer or a neurological disorder (e.g., Parkinson's disease, Alzheimer's, etc.). For example, in some embodiments a drug may be delivered by convection-enhanced delivery which establishes a pressure gradient at the tip of an intraparenchymal microcatheter inserted into the brain. The establishment of the pressure gradient by the microcatheter exploits bulk flow through the interstitial spaces of the brain. However, this bulk flow may be slow and may by itself be insufficient to provide therapeutically effective doses throughout the target tissue. Thus, in some embodiments, ultrasound may be applied to increase the rate of dispersion of the drug within the brain tissue according to methods and systems disclosed herein. The ultrasound may be delivered transcutaneously or coupled with the microcatheter (e.g., at a distal end or at a proximal end). Accordingly, in some embodiments, transcutaneous ultrasound into the head may be provided to disperse therapeutic agents into the tissue. A segmented or phased array transducer may be used to direct the sound to the desired region to avoid scattering by the skull. Dispersion at the desired region may be detected by changes in the acoustic response returned from the tissue.

In some embodiments, the tissue is inflamed. In some embodiments, the therapeutic agent comprises an antiviral agent or antifungal agent. In some embodiments, the tissue is infected. In some embodiments, the tissue may be colonized by microorganisms and treatment to reduce or eliminate microbial bioburden and biofilm may accelerate healing. For example, in some embodiments, the mixed flora and biofilm colonization may inhibit healing and may be associated with a chronic inflammatory response. Treatment of the colonization may relieve the chronic inflammation. Accordingly, the therapeutic agent can comprise an antibiotic. The antibiotic is not limited in any way and may be selected based on the specific circumstances, such as the type of infection present, for example causal bacteria by culture, tissue type, patient allergies, and the like. In some embodiments, the therapeutic agent comprises Cefazolin. In some embodiments, the therapeutic agent comprises Vancomycin. In some embodiments, the therapeutic agent comprises a cephalosporin antibiotic, for example, 7-ACA, Carbacephem, Cefacetrile, Cefaclor, Cefadroxil, Cefalexin, Cefaloglycin, Cefalonium, Cefalotin, Cefamandole, Cefapirin, Cefatrizine, Cefazaflur, Cefazedone, Cefazolin, Cefbuperazone, Cefcapene, Cefclidine, Cefdaloxime, Cefdinir, Cefditoren, Cefepime, Cefetamet, Cefixime, Cefluprenam, Cefmatilen, Cefmenoxime, Cefmetazole, Cefminox, Cefodizime, Cefonicid, Cefoperazone, Ceforanide, Cefoselis, Cefotaxime, Cefotetan, Cefotiam, Cefovecin, Cefoxitin, Cefozopran, Cefpimizole, Cefpiramide, Cefpirome, Cefpodoxime, Cefprozil, Cefquinome, Cefradine, Cefroxadine, Cefsulodin, Ceftaroline fosamil, Ceftazidime, Cefteram, Ceftezole, Ceftibuten, Ceftiofur, Ceftiolene, Ceftizoxime, Ceftobiprole, Ceftriaxone, Cefuroxime, Cefuzonam, Cephaloridine, Cephalosporin C, Cephamycin, Flomoxef, Latamoxef, or Loracarbef. In some embodiments, at least one of the antibiotics comprises Cipro and/or clinimycin. In some embodiments, the antibiotic comprises a penicillin family antibiotic, for example penicillin, amoxicillin, amplicillin, diclxacillin, oxacillin, penicillin V, piperacillin, piperacillin and tazobactum (Zosyn™). In some embodiments the antibiotic comprises a beta-lactam antibiotic.

In some embodiments the therapeutic agent is provided in solution or in a suspension. In some embodiments, the therapeutic agent is formulated according to conventional pharmaceutical practice as described in *Remington's Pharmaceutical Sciences* (18$^{th}$ ed, Mack Publishing Company, Easton, Pa., 1990). In some embodiments the therapeutic agent is provided in injectable form. In some embodiments the therapeutic agent is infusible. In some embodiments, the therapeutic agent is provided in a stable form for storage, for example lyophilized, and reconstituted prior to use. By way of example, suitable isotonic solutions for dissolving a therapeutic agent may be useful for infusion or injection in accordance with some embodiments herein, for example, saline or ringer's lactate, with the optional addition of epinephrine or xylocaine. Optionally, the tumescent fluid may be a hypotonic or hypertonic fluid.

In some embodiments, the therapeutic agent comprises an excipient. Excipients in accordance with some embodiments herein include but are not limited to antiadherents, binders, coatings, disintegrants, fillers and diluents, lubricants, glidants, preservatives, and sorbents. In some embodiments, the therapeutic agent comprises one or more active ingredients and one or more excipients. In some embodiments the therapeutic agent is packaged in a carrier. For example, the therapeutic agent can be packaged in liposomes or vesicles. In some embodiments, the therapeutic agent is not packaged in any carrier, liposomes, or vesicles. For example, the therapeutic agent can be dissolved or suspended in solution. Accordingly, in some embodiments, the method includes dissolving the therapeutic agent in solution if it is not already dissolved. In some embodiments, therapeutic agent is contacted with a solution for administration. In some embodiments, therapeutic agent and salts and/or lyophilized components of a solution to be administered are contacted with a solvent, for example sterile water or saline.

Appropriate therapeutic agents or combinations of therapeutic agents can be selected by the skilled artisan, based on a variety of factors, for example characteristics of the subject, disease state, disease progression, other medications or therapeutic agents being used by the patient, allergies, and the like.

Subjects

Systems and methods in accordance with embodiments herein can be useful for administration of therapeutic agents to a variety of subjects. In some embodiments, a system or method as provided herein is configured to administer therapeutic agent to any of a variety of subjects. In some embodiments, the system or method is configured to administer therapeutic agent to a particular type or category of subject, for example subjects of a particular species and/or particular clinical indication.

In some embodiments, the subject is a human. In some embodiments, the subject is a patient in need of treatment. In some embodiments, the subject is a non-human animal. In some embodiments, the subject is a non-human mammal, for example a cow, horse, sheep, pig, goat, dog or cat. In some embodiments, the subject is a non-human primate.

In some embodiments, the subject is characterized by at least one tissue having limited blood supply that is in need of treatment with a therapeutic agent. In some embodiments, the subject has an infection in a tissue having limited blood supply. By way of example, diabetic subjects can be characterized by limited blood supply to one or more sites of infection. Accordingly, in some embodiments, the subject is diabetic. By way of example, some tumors can have low blood supply. Accordingly, in some embodiments, the subject has a tumor, and therapeutic agent is administered at, near, or above the site of the tumor.

In some embodiments, the subject has a target tissue that is not characterized by a low blood supply, but the tissue is in need of a treatment with a therapeutic agent at a concentration that would be deleterious if delivered systemically. Accordingly, systems and methods according to some embodiments herein can disperse a therapeutic agent (for example antibiotic) in a target tissue regardless of whether the target tissue has a low blood supply.

In some embodiments, the subject is at risk of developing a disease state, for example an infection. Accordingly, in some embodiments, systems and methods in accordance with some embodiments herein can administer therapeutic agent prophylactically. In some embodiments, the systems and/or methods can be used to disperse an antibiotic in a target tissue prior to surgery in order to help prevent infection.

Concentrations and Doses of Therapeutic Agent

It has been observed that when a therapeutic agent is administered intravenously, the concentration of therapeutic agent in serum is higher than the concentration in the target tissue, especially if the target tissue has limited blood supply. Without being limited by any theory, it is contemplated that in accordance with some embodiments herein, following administration of therapeutic agent at or near a target tissue, the application of ultrasound energy results in efficient dispersal of the therapeutic agent in the target tissue, and can yield substantially greater concentrations and/or amounts of therapeutic agent in the target tissue than will be yielded by intravenous administration. Accordingly, in some embodiments, the system is configured to disperse all or substantially all of the administered therapeutic agent in the target tissue. In some embodiments, immediately following, or within 1-2 hours of administration of ultrasound energy, the concentration of therapeutic agent in the target tissue is at least 10× the concentration in the serum, for example at least about 10×, 20×, 50×, 100×, 200×, 500×, 700×, 1000×, 2000×, 3000×, 4000×, 5000×, or 10,000× or greater, including ranges between any two of the listed values. As such, in some embodiments, at least a therapeutically effective concentration and amount of therapeutic agent is administered to the subject.

A variety of doses and concentrations of therapeutic agent can be used in conjunction with embodiments herein. Without being limited by any theory, it is contemplated that systems in accordance with embodiments herein can deliver therapeutic agents at a target tissue or in the vicinity of the target tissue, and as such can be administered at, near, or above therapeutically-effective concentrations, even if the these concentrations would be undesirable or deleterious if administered through other routes. For example, while a particular concentration of therapeutic agent might be effective when present locally at a target tissue, that same concentration might be toxic or lethal if present systemically. Additionally, for some routes of administration (for example intravenous or oral), the concentration of therapeutic agent required to achieve an effective concentration of therapeutic agent in the target tissue may result in an undesirably high systemic concentration of the therapeutic agent. Accordingly, systems and methods in accordance with some embodiments herein can minimize or avoid undesirable effects of high systemic concentrations, while achieving a useful local concentration of therapeutic agent in the target tissue.

In some embodiments, the system or method is configured to administer a therapeutically effective amount of therapeutic agent to the target tissue at 50% or more of a concentration that would be lethal if administered systemically, for example at least 50%, 60%, 70%, 80%, 90%, 100%, 150%, 200%, 250%, 300%, 350%, 400%, 450%, 500%, 600%, 700%, 800%, 900%, 1000%, 1500%, 2000%, 3000%, 4000%, 5000%, 6000%, 7000%, 8000%, 9000%, or 10,000% of the concentration that would be lethal if present systemically, including ranges between any two of the listed values.

In some embodiments, the system or method is configured to administer a therapeutically effective amount of therapeutic agent to the target tissue a therapeutic agent at a concentration of at least 10× greater than the maximum concentration that can be administered intravenously, for example at least 10×, 20×, 50×, 100×, 200×, 500×, 700×, 1000×, 2000×, 3000×, 4000×, 5000×, or 10,000× or greater, including ranges between any two of the listed values. The skilled artisan will appreciate that the actual maximum concentration of the therapeutic agent can depend on the therapeutic agent and/or subject. For example, the skilled artisan may look to the label of the therapeutic agent to determine the maximum concentration.

After injection, and prior to ultrasound application, the fluid may be pooled in rivulets within the tissue. These rivulets of therapeutic agent are generally unable to treat an infection because the drug stays only in these pools. By dispersing the drug using ultrasound, or atomized through the tissue, its surface to volume ratio increases and it comes into contact with many more pathogenic cells. Normally, the body atomizes the drug by first collecting it into the circulatory system and then delivering it molecule by molecule via diffusion to the body tissue. The circulatory fed dispersion is good at dispersion but dramatically lowers the concentration because the circulatory system delivers the drug to the entire body. Accordingly, ultrasonic dispersion of the rivulets or pooled fluid with therapeutic agents may increase the surface area without dilution by the entire body. In some embodiments, the system or method is configured to administer an therapeutic agent, for example a beta-lactam antibiotic such as Cefazolin, at a concentration of at least about 1,000 µg/ml subcutaneously, for example about 1,000 µg/ml to about 20,000 µg/ml or more, about 1,000 µg/ml to about 10,000 µg/ml, about 1,000 µg/ml to about 5,000 µg/ml, about 1,000 µg/ml to about 2,000 µg/ml, about 2,000 µg/ml to about 20,000 µg/ml, about 2,000 µg/ml to about 10,000 µg/ml, about 2,000 µg/ml to about 5,000 µg/ml, about 5,000 µg/ml to about 20,000 µg/ml, or about 5,000 µg/ml to about 10,000 µg/ml. After dispersion by ultrasound delivery, the injected fluid may permeate throughout the target tissue to impregnate the target tissue with concentrations therapeutic agents described above.

Administration of Therapeutic Agent

Systems in accordance with embodiments herein can be configured to administer therapeutic agent from the container directly or indirectly to a subject. In some embodiments, the container is in fluid communication with a tissue interface as described herein. In some embodiments, the system comprises a pump in fluid communication with the container and tissue interface, and configured to control the flow of solution from the container and through the tissue interface into the subject, and thus control the flow of solution comprising therapeutic agent from the system to the subject. In some embodiments, the pump is configured for manual control. In some embodiments, the pump is configured to administer solution comprising therapeutic agent at a desired rate, which can be set by an operator. In some embodiments, the pump is under the control of a processor. The processor can be configured to automatically control the operation of the pump. In some embodiments, the processor comprises an electronic processor. In some embodiments, the processor dynamically controls the rate and/or pressure at which the pump administers solution comprising therapeutic agent, for example in response to feedback signals from an acoustic sensor as described herein. In some embodiments, the pump adjusts its output in response to the sensor in real time. For example, the amount of power and/or the rate or amount of solution injected may be determined by the size and depth of the tissue being treated. These tissues can vary as comparing an ankle with a thigh. In some embodiments, the pump adjusts its output in response to a signal detected by the sensor in less than 0.5 seconds after the sensor detects the signal, for example less than 0.5, 0.2, 0.1, 0.05, or 0.01 seconds.

The pump can be configured to control the administration rate of solution comprising therapeutic agent. In some embodiments, the pump is configured to increase or decrease its output so as to administer fluid from the container to the subject (via the tissue interface) at a desired flow rate. In some embodiments, the desired flow rate is at least about 0.5 ml/minute, for example about 0.5 ml/minute, 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, 45, 46, 47, 48, 49, or 50 ml/minute, including ranges between any two of the listed values. In some embodiments, the desired flow rate is about 0.5 ml/minute-20 ml/minute, for example about 0.5 ml/minute-10 ml/minute, about 0.5 ml/minute-5 ml/minute, about 1 ml/minute-20 ml/minute, about 1 ml/minute-10 ml/minute, about 1 ml/minute-5 ml/minute, about 5 ml/minute-20 ml/minute, or about 5 ml/minute-10 ml/minute.

In some embodiments, the pump comprises a peristaltic pump. In some embodiments, the pump comprises a piston pump.

Microstreaming and Gasses

Without being limited by any theory, it is contemplated that administration of ultrasound energy at the site of therapeutic agent administration in a subject in accordance with some embodiments herein can efficiently disperse the therapeutic agent to a target tissue through microstreaming in liquid in the subject. In some embodiments the ultrasound energy can be administered less than 5 minutes after subcutaneous injection of the delivery fluid, less than 3 minutes after injection of the delivery fluid, or sooner (e.g., within 1 minute of injection. Optionally, the ultrasound energy may be applied simultaneously with the injection procedure. In some embodiments, amounts of microstreaming can be affected by processes that affect negative pressure, friction, and/or cavitation. For example, friction along a flow path can increase an amount of cavitation, so as to produce "friction cavitation." Furthermore, without being limited by any theory, it is contemplated that a number of fluid-containing tissues in a subject can comprise a number of interstitial channels, which are affected non-linearly by a variety of factors, for example negative pressure. It is further contemplated that even if the partial pressure of gas in liquid itself is too weak to induce cavitation, the negative pressure can affect the state of the interstitial channels, and thus indirectly can affect microstreaming. Accordingly, it is contemplated herein that amounts of microstreaming and/or cavitation (and thus dispersion of therapeutic agent in tissue) can be regulated in accordance with some embodiments herein by regulating amounts of cavitation, friction, and/or negative pressure. Without being limited by any theory, it is contemplated that the amount of microstreaming and/or cavitation is proportional to the partial pressure of dissolved gas in a liquid subjected to ultrasound energy. As such, in some embodiments the partial pressure of dissolved gas in a liquid can be adjusted in order to tune the amount of microstreaming and/or cavitation that occurs in the subject, which can in turn affect the amount of dispersal of therapeutic agent in the tissue. In some cases it may be necessary to increase the strength of the sound field at which cavitation occur. The pressure of the dissolved gas may be lowered so as to force the cavitation to take place at higher amplitudes and in turn, be stronger. This may be desirable when the interstitial spaces are more dense or have less flexibility or permeability. Suppression of cavitation to higher sound field levels may increase other microstreaming capabilities off the sound field. In some embodiments, inert gas/and or negative pressure is applied to liquid comprising therapeutic agent prior to administration so as to achieve a desired range of partial pressure of gas in the liquid and achieve a desired amount of microstreaming and/or cavitation in the subject. In some embodiments, inert gas is applied to liquid comprising therapeutic agent prior to administration so as to achieve a desired amount of microstreaming and/or cavitation in the subject. In some embodiments, negative pressure is applied to liquid comprising therapeutic agent prior to administration so as to achieve a desired amount of microstreaming and/or cavitation in the subject. In some embodiments, a combination of inert gas and negative pressure are applied to liquid comprising therapeutic agent prior to administration so as to achieve a desired amount of microstreaming and/or cavitation in the subject. In some embodiments, the inert gas and negative pressure are applied alternatingly. In some embodiments, the inert gas and negative pressure are applied alternatingly and sequentially. In some embodiments, the inert gas and negative pressure are applied simultaneously. Thus, in some embodiments the delivery of therapeutic agent can be tuned for a desired concentration of therapeutic agent in the target tissue.

Solution administered to the subject can comprise any of a number of gasses that can affect the amount of microstreaming in accordance with some embodiments. In some embodiments, the solution comprises a combination of two or more gasses. Without being limited by any theory, it is contemplated that inert gasses are less likely than reactive gasses to induce side effects upon administration to the subject. Accordingly, in some embodiments, the solution comprises at least one inert gas. In some embodiments, a mixture of two or more inert gasses is provided. In some embodiments, the inert gas comprises a group 8A element, for example helium, neon, argon, krypton, xenon, or radon. In some embodiments, the inert gas comprises argon. In some embodiments, the inert gas comprises nitrogen. It is noted that while reference is made herein to inert gas, it is also possible for solutions in accordance with some embodiments herein to contain small or trace amounts of other gasses, including non-inert gasses.

Systems in accordance with embodiments herein can be configured for controlling the partial pressure of inert gas in the solution comprising therapeutic agent. The system can comprise a source of inert gas, for example a canister. In some embodiments the source of inert gas is detachable form the system, for example to facilitate attachment of a canister comprising a desired inert gas, or to facilitate replacement of empty canisters. In some embodiments, the source of inert gas is in gas communication with a container in the system. In some embodiments, the container is configured to mix the inert gas with solution comprising therapeutic agent. In some embodiments, the container is free, or is substantially free of other gasses, so that a total pressure in the chamber can serve as a proxy for partial pressure of inert gas. In some embodiments, the container is purged of other gasses, for example with a vacuum, prior to application of the inert gas.

In some embodiments, the container comprises a meter such as a pressure gauge for monitoring the partial pressure of gas in the solution, so that a user may apply desired partial pressure of inert gas to the solution, for example, applying additional inert gas and/or a vacuum until a desired partial pressure of inert gas is achieved. For example, in some embodiments, an operator can open a valve positioned between the source of inert gas and the container, while closing a valve positioned between the vacuum and the container (and/or turn off the vacuum), and can turn on a solution mixer. The operator can continue to add inert gas and mix until the partial pressure of inert gas is raised to a desired level. Optionally, the operator can first use the vacuum to purge the container of other gasses prior to or concurrently with adding inert gas. In some embodiments, the operator can close a valve between the container and the source of inert gas, and can open a valve between the container and the vacuum so as to bleed off inert gas until the partial pressure of inert gas is lowered to a desired level. In some embodiments, the solution is mixed or agitated so as to dissolve the inert gas therein. In some embodiments, the system is configured to automatically to add or remove gas so as to arrive at a particular partial pressure of gas in the solution. In some embodiments, the partial pressure of inert gas is set to a set point, and the system is configured to automatically maintain the partial pressure at the set point.

In some embodiments, an operator selects a desired partial pressure (or range of partial pressures), and sets the system to provide the partial pressure of inert gas in the solution in the container at that desired partial pressure (or within the desired range). In some embodiments, the operator can optionally adjust the partial pressure from procedure to procedure. In some embodiments, the system is configured to place the partial pressure of the inert gas at 25° C. in the range of about 1 kPa to about 500 kPa, for example about 1 kPa to about 400 kPa, about 1 kPa to about 300 kPa, about 1 kPa to about 200 kPa, about 1 kPa to about 150 kPa, about 1 kPa to about 100 kPa, about 1 kPa to about 70 kPa, about 1 kPa to about 50 kPa, about 1 kPa to about 30 kPa, about 1 kPa to about 20 kPa, about 1 kPa to about 10 kPa, about 1 kPa to about 5 kPa, about 3 kPa to about 500 kPa, about 3 kPa to about 400 kPa, about 3 kPa to about 300 kPa, about 3 kPa to about 200 kPa, about 3 kPa to about 150 kPa, about 3 kPa to about 100 kPa, about 3 kPa to about 70 kPa, about 3 kPa to about 50 kPa, about 3 kPa to about 30 kPa, about 3 kPa to about 20 kPa, about 3 kPa to about 10 kPa, about 3 kPa to about 5 kPa, about 5 kPa to about 500 kPa, about 5 kPa to about 400 kPa, about 5 kPa to about 300 kPa, about 5 kPa to about 200 kPa, about 5 kPa to about 150 kPa, about 5 kPa to about 100 kPa, about 5 kPa to about 70 kPa, about 5 kPa to about 50 kPa, about 5 kPa to about 30 kPa, about 5 kPa to about 20 kPa, about 5 kPa to about 10 kPa, about 10 kPa to about 500 kPa, about 10 kPa to about 400 kPa, about 10 kPa to about 300 kPa, about 10 kPa to about 200 kPa, about 10 kPa to about 150 kPa, about 10 kPa to about 100 kPa, about 10 kPa to about 70 kPa, about 10 kPa to about 50 kPa, about 10 kPa to about 30 kPa, about 10 kPa to about 20 kPa, about 50 kPa to about 500 kPa, about 50 kPa to about 400 kPa, about 10 kPa to about 300 kPa, about 50 kPa to about 200 kPa, about 50 kPa to about 150 kPa, about 50 kPa to about 100 kPa, about 100 kPa to about 500 kPa, about 100 kPa to about 400 kPa, about 100 kPa to about 300 kPa, about 100 kPa to about 200 kPa, or about 100 kPa to about 150 kPa. Exemplary partial pressure of inert gas that can be used in accordance with some embodiments herein include, but are not limited to about 1 kPa, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 30, 440, 450, 460, 470, 480, 490, 500 kPa, or more, including ranges between any two of the listed values. It is noted that temperature can affect the partial pressure of gas, and as such, the indicated temperature of 25° C. is provided for a reference point only, and does not necessitate that the solution be at 25° C. It is noted that a solution having a particular partial pressure at 25° C. may have a different partial pressure at a different temperature (assuming other parameters remain constant), but that the particular partial pressure at 25° C. would still be a characteristic of the solution. The range of partial pressures at which gas is dissolved into the injectant fluid may range from 100 Pa to 200 kPA in some embodiments.

Ultrasound Applicators

Ultrasound applicators can be used in accordance with embodiments herein. In some embodiments, the ultrasound applicator comprises an ultrasound transducer. A variety of suitable ultrasound applicators are known to the skilled artisan, and can be selected based the particular application, for example the type of subject, type of therapeutic agent, and/or location of administering the therapeutic agent. Exemplary ultrasound applicators sand generator systems that can be used in conjunction with some embodiments herein include Mettler Electronics Sonicator™ series ultrasound devices (e.g. Sonicator™ 715, 716, 740, 740×), Mettler Electronics Sonicators Plus™ series ultrasound devices (e.g. Sonicator Plus™ 930, 940, 992, and 994), US Pro 2000™ portable ultrasound device, Chattanooga Inetlect TransPort™ ultrasound units, SoundCare™ plus ultrasound units, other available ultrasound units configured for output at about 1 MHz to about 3 MHz or more, and modifications thereof. In some embodiments, the ultrasound applicator comprises a handheld applicator. In some embodiments, the ultrasound applicator comprises a wand. In some embodiments, the ultrasound applicator comprises a catheter. In some embodiments, the system is configured to be compatible with any of a number of ultrasound applicators, depending on the desired use. In some embodiments, the ultrasound applicator is configured for transcutaneous or transdermal application of ultrasound energy. In some embodiments, the ultrasound applicator is configured to apply ultrasonic energy directly to the target tissue. In some embodiments, the ultrasound applicator is configured to apply ultrasonic energy near the target tissue, for example within 20 cm, 19 cm, 18 cm, 17 cm, 16 cm, 15 cm, 14 cm, 13 cm, 12 cm, 11 cm, 10 cm, 9 cm, 8 cm, 7 cm, 6 cm, 5 cm, 4 cm, 3 cm, 2 cm, 1 cm, or 0.5 cm of the target tissue, including ranges between any two of the listed values.

In some embodiments, the ultrasound applicator is operatively connected to an ultrasound generator. A variety of ultrasound generators are known to the skilled artisan, including ultrasound generators of the exemplary ultrasound systems described above and modifications thereof, An ultrasound generator having suitable performance characteristics (for example suitable power levels and ranges of ultrasound frequency) can be selected by the skilled artisan.

In some embodiments, the ultrasound applicator (alone or in conjunction with an ultrasound generator) is configured to deliver ultrasonic energy transcutaneously at a frequency of about 10 kHz to about 10 MHz and a power density of 0.5 to about 20 watts/cm$^2$. In some embodiments, the ultrasound applicator and/or generator are configured to deliver ultrasonic energy transcutaneously at a frequency of about 20 kHz to about 5 MHz. In some embodiments, the ultrasound applicator and/or generator are configured to deliver ultrasonic energy transcutaneously at a power density of about 1 watt/cm$^2$ to about 10 watts/cm$^2$. In some embodiments, the ultrasound applicator and/or generator are configured to deliver ultrasonic energy transcutaneously at a frequency of about 20 kHz to about 5 MHz and a power density of 1 to about 5 watts/cm$^2$, for example a frequency of about 20 kHz to about 5 MHz and a power density of about 1 to about 10 watts/cm$^2$; a frequency of about 20 kHz to about 5 MHz and a power density of about 2 to about 10 watts/cm$^2$; a frequency of about 20 kHz to about 5 MHz and a power density of about 3 to about 10 watts/cm$^2$; a frequency of about 20 kHz to about 5 MHz and a power density of about 4 to about 10 watts/cm2; a frequency of about 20 kHz to about 5 MHz and a power density of about 5 to about 10 watts/cm$^2$; a frequency of about 20 kHz to about 5 MHz and a power density of about 2 to about 5 watts/cm$^2$; a frequency of about 20 kHz to about 5 MHz and a power density of about 3 to about 5 watts/cm$^2$; a frequency of about 20 kHz to about 5 MHz and a power density of about 4 to about 5 watts/cm$^2$; a frequency of about 20 kHz to about 5 MHz and a power density of about 1 to about 4 watts/cm$^2$; a frequency of about 20 kHz to about 5 MHz and a power density of about 1 to about 3 watts/cm$^2$; a frequency of about 20 kHz to about 5 MHz and a power density of about 1 to about 2 watts/cm$^2$; a frequency of about 100 kHz to about 5 MHz and a power density of about 1 to about 10 watts/cm$^2$; a frequency of about 100 kHz to about 5 MHz and a power density of about 2 to about 10 watts/cm$^2$; a frequency of about 100 kHz to about 5 MHz and a power density of about 3 to about 10 watts/cm$^2$; a frequency of about 100 kHz to about 5 MHz and a power density of about 4 to about 10 watts/cm2; a frequency of about 100 kHz to about 5 MHz and a power density of about 5 to about 10 watts/cm$^2$; a frequency of about 100 kHz to about 5 MHz and a power density of about 1 to about 5 watts/cm$^2$; a frequency of about 100 kHz to about 5 MHz and a power density of about 2 to about 5 watts/cm$^2$; a frequency of about 100 kHz to about 5 MHz and a power density of about 3 to about 5 watts/cm$^2$; a frequency of about 100 kHz to about 5 MHz and a power density of about 4 to about 5 watts/cm$^2$; a frequency of about 100 kHz to about 5 MHz and a power density of about 1 to about 4 watts/cm$^2$; a frequency of about 100 kHz to about 5 MHz and a power density of about 1 to about 3 watts/cm$^2$; a frequency of about 100 kHz to about 5 MHz and a power density of about 1 to about 2 watts/cm$^2$; a frequency of about 1 MHz to about 5 MHz and a power density of about 1 to about 10 watts/cm$^2$; a frequency of about 1 MHz to about 5 MHz and a power density of about 2 to about 10 watts/cm$^2$; a frequency of about 1 MHz to about 5 MHz and a power density of about 3 to about 10 watts/cm$^2$; a frequency of about 1 MHz to about 5 MHz and a power density of about 4 to about 10 watts/cm2; a frequency of about 1 MHz to about 5 MHz and a power density of about 5 to about 10 watts/cm$^2$; a frequency of about 1 MHz to about 5 MHz and a power density of about 1 to about 5 watts/cm$^2$; a frequency of about 1 MHz to about 5 MHz and a power density of about 2 to about 5 watts/cm$^2$; a frequency of about 1 MHz to about 5 MHz and a power density of about 3 to about 5 watts/cm$^2$; a frequency of about 1 MHz to about 5 MHz and a power density of about 4 to about 5 watts/cm$^2$; a frequency of about 1 MHz to about 5 MHz and a power density of about 1 to about 4 watts/cm$^2$; a frequency of about 1 MHz to about 5 MHz and a power density of about 1 to about 3 watts/cm$^2$; a frequency of about 1 MHz to about 5 MHz and a power density of about 1 to about 2 watts/cm$^2$; a frequency of about 20 kHz to about 2 MHz and a power density of about 1 to about 10 watts/cm$^2$; a frequency of about 20 kHz to about 2 MHz and a power density of about 2 to about 10 watts/cm$^2$; a frequency of about 20 kHz to about 2 MHz and a power density of about 3 to about 10 watts/cm$^2$; a frequency of about 20 kHz to about 2 MHz and a power density of about 4 to about 10 watts/cm2; a frequency of about 20 kHz to about 2 MHz and a power density of about 5 to about 10 watts/cm$^2$; a frequency of about 20 kHz to about 2 MHz and a power density of about 1 to about 5 watts/cm$^2$; a frequency of about 20 kHz to about 2 MHz and a power density of about 2 to about 5 watts/cm$^2$; a frequency of about 20 kHz to about 2 MHz and a power density of about 3 to about 5 watts/cm$^2$; a frequency of about 20 kHz to about 2 MHz and a power density of about 4 to about 5 watts/cm$^2$; a frequency of about 20 kHz to about 2 MHz and a power density of about 1 to about 4 watts/cm$^2$; a frequency of about 20 kHz to about 2 MHz and a power density of about 1 to about 3 watts/cm$^2$; a frequency of about 20 kHz to about 2 MHz and a power density of about 1 to about 2 watts/cm$^2$; a frequency of about 20 kHz to about 1 MHz and a power density of about 1 to about 10 watts/cm$^2$; a frequency of about 20 kHz to about 1 MHz and a power density of about 2 to about 10 watts/cm$^2$; a frequency of about 20 kHz to about 1 MHz and a power density of about 3 to about 10 watts/cm$^2$; a frequency of about 20 kHz to about 1 MHz and a power density of about 4 to about 10 watts/cm2; a frequency of about 20 kHz to about 1 MHz and a power density of about 5 to about 10 watts/cm²; a frequency of about 20 kHz to about 1 MHz and a power density of about 1 to about 5 watts/cm²; a frequency of about 20 kHz to about 1 MHz and a power density of about 1 to about 5 watts/cm²; a frequency of about 20 kHz to about 1 MHz and a power density of about 2 to about 5 watts/cm²; a frequency of about 20 kHz to about 1 MHz and a power density of about 3 to about 5 watts/cm²; a frequency of about 20 kHz to about 1 MHz and a power density of about 4 to about 5 watts/cm²; a frequency of about 20 kHz to about 1 MHz and a power density of about 1 to about 4 watts/cm²; a frequency of about 20 kHz to about 1 MHz and a power density of about 1 to about 3 watts/cm²; or a frequency of about 20 kHz to about 1 MHz and a power density of about 1 to about 2 watts/cm². In some embodiments, a smaller diameter transducer may be used which will allow access to regions of the foot area. In some embodiments, the ultrasound applicator and/or generator are further configured to provide ultrasound energy at powers and/or densities outside of the stated ranges.

In some embodiments, the ultrasound applicator and/or ultrasound generator are configured to pulse the ultrasound energy. In some embodiments, a suitable pulse duration and frequency are selected by an operator. In some embodiments, a pulse of ultrasound energy having a duration of about 0.1 second to about 20 seconds is provided, for example about 0.1 to about 20 seconds, about 0.1 to about 10 seconds, about 0.1 to about 5 seconds, about 0.1 to about 2 seconds, about 0.1 to about 1 second, about 0.1 to about 0.5 seconds, about 0.2 to about 20 seconds, about 0.2 to about 10 seconds, about 0.2 to about 5 seconds, about 0.2 to about 2 seconds, about 0.2 to about 1 second, about 0.2 to about 0.5 seconds, about 0.5 to about 20 seconds, about 0.5 to about 10 seconds, about 0.5 to about 5 seconds, about 0.5 to about 2 seconds, about 0.5 to about 1 second, about 1 to about 20 seconds, about 1 to about 10 seconds, about 1 to about 5 seconds, about 1 to about 2 seconds, about 2 to about 20 seconds, about 2 to about 10 seconds, about 2 to about 5 seconds, about 5 to about 20 seconds, or about 5 to about 10 seconds. In some embodiments, the duration between pulses is at least about 0.5 seconds, for example, at least about 0.5 seconds, 1, 2, 3, 4, 5, 6, 7, 8, 9, 10, 15, 20, 25, 30, 35, 40, 45, 50, 55, 60, 65, 70, 75, 80, 85, or 90 seconds, including ranges between any two of the listed values. In some embodiments, the ultrasound applicator is configured to pulse ultrasound energy for about 0.1 to 20 seconds at a pulse frequency of about 2-100 pulses per minute, for example about 0.1 to 20 seconds at a pulse frequency of about 2-100 pulses per minute, about 1 to 20 seconds at a pulse frequency of about 2-100 pulses per minute, about 0.1 to 10 seconds at a pulse frequency of about 2-100 pulses per minute, about 0.1 to 5 seconds at a pulse frequency of about 2-100 pulses per minute, about 1 to 20 seconds at a pulse frequency of about 2-50 pulses per minute, about 0.1 to 10 seconds at a pulse frequency of about 2-50 pulses per minute, about 0.1 to 5 seconds at a pulse frequency of about 2-50 pulses per minute, about 1 to 20 seconds at a pulse frequency of about 2-10 pulses per minute, about 0.1 to 10 seconds at a pulse frequency of about 2-10 pulses per minute, or about 0.1 to 5 seconds at a pulse frequency of about 2-10 pulses per minute.

In some embodiments, the ultrasound applicator and/or ultrasound generator are in data communication with a controller for turning the application of ultrasound energy on and off. In some embodiments, the controller comprises a foot pedal, trigger, button, or dial.

It is noted that for some subjects, relatively high and prolonged ultrasound output can induce burning of tissue at or near the site of ultrasound energy administration, or otherwise can induce tissue damage. Accordingly, in some embodiments, the ultrasound duty cycle is chosen to minimize likelihood of burning, and also to minimize power applied relative to effective penetration of the therapeutic agent into the target tissue.

In some embodiments, the ultrasound applicator and/or ultrasound generator are in communication with a1 processor. The processor can control the duty cycle of the ultrasound applicator, for example by controlling the frequency, energy, and/or pulse parameters of the ultrasound energy administered. In some embodiments, the processor adjusts the ultrasound duty cycle in response to feedback from a sensor as described herein. In some embodiments, the processor adjusts the ultrasound duty cycle in response to the sensor in real time. In some embodiments, the processor adjusts the ultrasound duty cycle in response to a signal detected by the sensor in less than 0.5 seconds after the sensor detects the signal, for example less than 0.5, 0.2, 0.1, 0.05, or 0.01 seconds. In some embodiments, the processor is selected to provide a minimum ultrasound energy and/or frequency so as to effectively disperse the therapeutic agent in the target tissue, while minimizing a risk of tissue damage (e.g. burning) due to ultrasound energy. In some embodiments, a power and/or frequency may be gradually increased until cavitation/microstreaming is detected. At that point, the power and/or frequency may be held constant until cavitation/microstreaming is no longer detected. In other embodiments, a power and frequency may be used that is known to cause cavitation/microstreaming (e.g., as detected by an increased harmonic response). The response may be monitored during the application to determine the extent of dispersion. If a duration of the dispersion is shorter than expected, a sound level may be increased to see if a desired harmonic response is returned. Thereafter, the sound level may be held constant until the full dispersion. For example, in a case of cancer or the like, ultrasound may start at 3 W/cm². No harmonics in the acoustic response may be indicative of a lack of dispersion. Thereafter, the sound field may be increased and/or a frequency may be increased until a harmonics/subharmonic or broadband response is returned. At that point, the ultrasound may be applied until dispersion is complete.

Sensors

It is contemplated that delivery of therapeutic agent in accordance with some embodiments herein can be further enhanced by dynamically adjusting delivery parameters. Without being limited by any theory, it is contemplated that the amount of microstreaming and/or cavitation can be proportional to the amount of dispersal of therapeutic agent in the tissue. As such, in some embodiments, the amount of microstreaming and/or cavitation is increased so as to increase the amount of therapeutic agent being dispersed in a tissue. In some embodiments, the amount of microstreaming and/or cavitation is decreased so as to decrease the amount of therapeutic agent being dispersed in a tissue. For example, the ultrasound frequency and/or energy can be adjusted in response to the amount of microstreaming and/or cavitation that is occurring in the subject, for example to maintain a desired microstreaming and/or cavitation or a range of microstreaming and/or cavitation. For example, the rate of delivery of therapeutic agent can be adjusted in response to the amount of cavitation that is occurring in the subject. For example, the ultrasound frequency and/or energy and the rate of delivery of therapeutic agent from the container can be adjusted in response to the amount of cavitation that is occurring in the subject.

Accordingly, in some embodiments, the system comprises a sensor configured to sense the amount of microstreaming and/or cavitation in the subject. In some embodiments, the sensor is configured to measure the acoustic reaction of the subject. Without being limited by any theory, it is contemplated that even if the ultrasound transducer outputs ultrasound energy at a particular frequency, a range of frequencies can be receivable from the subject, including both broad band and harmonic and subharmonic frequencies. As such, in some embodiments, the measurement of acoustic reaction includes a broad band response. The broad band and harmonic response of the target tissue, the injected solution, and an interaction between the target tissue and the injected solution may be monitored by the sensor.

In some embodiments, the sensor comprises a sound-measuring transducer. In some embodiments, the transducer is configured to detect acoustic signals from a broad band. The measurements from the sound measuring transducer can then be processed, for example by subjecting the sensed signals to a Fast Fourier Transform (FFT) algorithm. The FFT-transformed signals can permit evaluation of the response of the body at a broad range of frequencies, for example all frequencies or substantially all frequencies. In some embodiments, the sensor is in data communication with a processor, and the processor processes the measurements, for example by applying the FFT. Optionally the FFT may be combined with a filter that blocks the input frequency. In some embodiments a spectrum analyzer may be used.

In some embodiments, the sensor is in data communication with a processor that controls the amount of induced microstreaming and/or cavitation in response to the acoustic reaction detected by the sensor. In some embodiments, the sensor is in wireless data communication with the processor. In some embodiments, the sensor is directly or indirectly wired to the processor. In some embodiments the processor is configured to adjust ultrasound parameters (frequency and/or power) in response to the amount of microstreaming and/or cavitation detected. For example, the processor can increase ultrasound power and/or frequency to increase the amount of microstreaming and/or cavitation, or can decrease the ultrasound power and/or frequency to decrease the amount of microstreaming and/or cavitation. In some embodiments, a particular set point for an amount of microstreaming and/or cavitation is selected by an operator. The set point can be based on a variety of factors, for example type of therapeutic agent, type of tissue for delivery, size of tissue, and the like. The processor can modulate the ultrasound parameters in response to the acoustic reaction in the subject so as to maintain microstreaming and/or cavitation at or near the set point. In some embodiments, the operator can set a threshold, so that microstreaming and/or cavitation do not fall below a certain threshold, or does not exceed a certain threshold. The threshold may be a point at which the broad band sound field and/or the subharmonics/extra harmonic energy are no longer present in the acoustic response. In some embodiments, the operator can set a range between two thresholds, so that microstreaming and/or cavitation do not fall below a certain threshold and does not exceed a certain threshold. In some embodiments, delivery of solution comprising therapeutic agent to the subject continues for a set amount of time at a desired microstreaming and/or cavitation level so as to achieve a therapeutically effective concentration of therapeutic agent in the subject.

In some embodiments, the ultrasound applicator comprises the sensor. In some embodiments, the sensor is mounted directly on the ultrasound applicator. In some embodiments, the sensor is separate from the ultrasound applicator, for example, so that the operator can hold the ultrasound applicator in one hand and the sensor in the other hand.

Figure 2A:
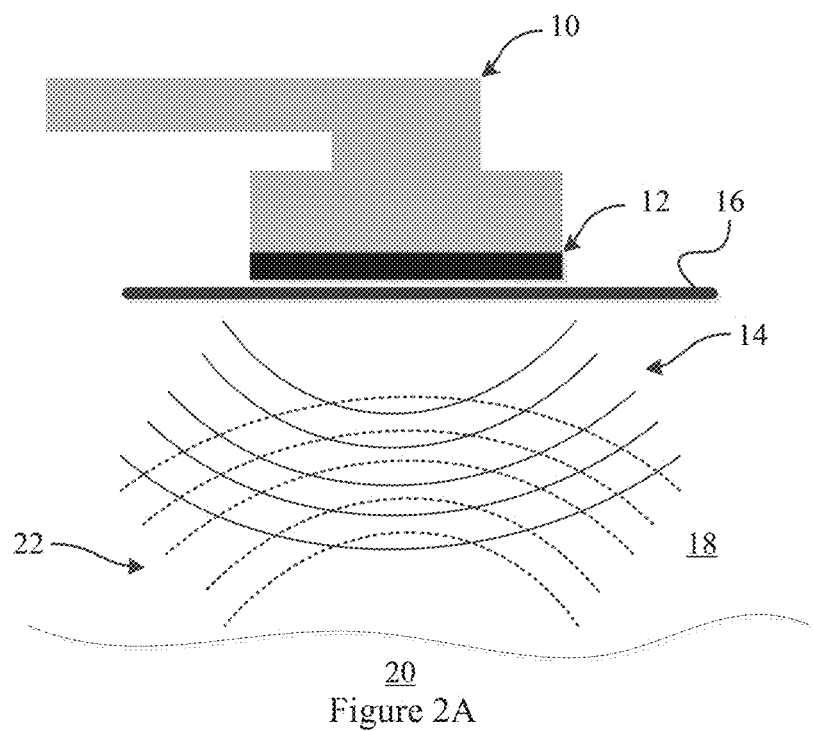
FIGS. 2A-2B illustrate an exemplary ultrasound delivery device configured to monitor an acoustic reaction according to some embodiments of the present invention.
Figure 2B:
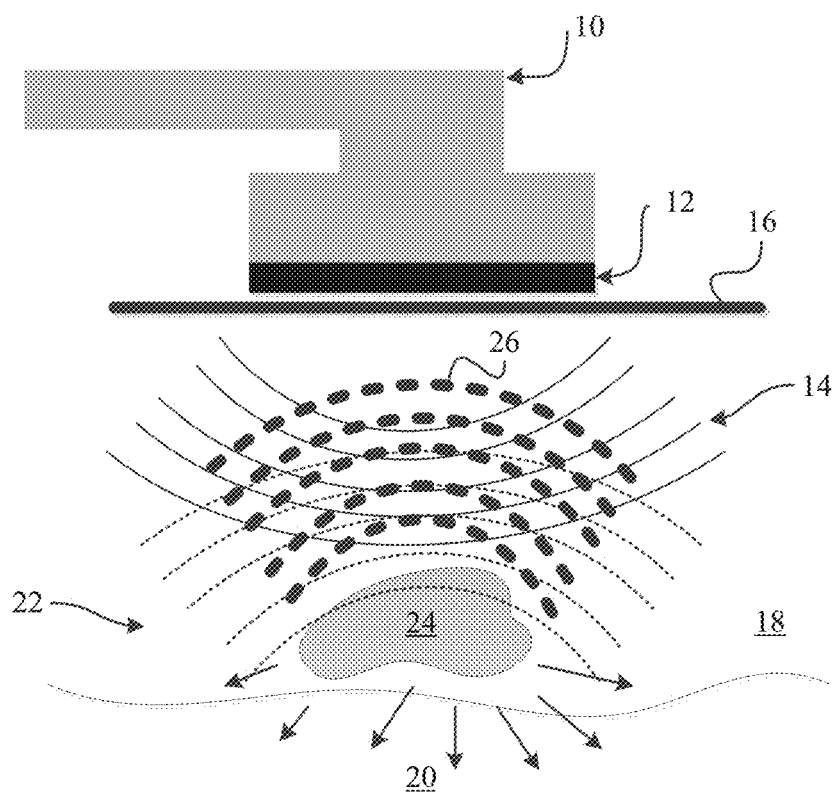

For example, FIGS. 2A-2B illustrate an exemplary ultrasound applicator 10 including an acoustic sensor 12 integrated therewith according to some embodiments of the invention. FIG. 2A illustrates ultrasound applicator 10 broadcasting ultrasound 14 across the surface 16 of the skin 18 of a patient toward a target tissue 20. In response to the broadcasted ultrasound 14, the target tissue 20 will emit an acoustic signal. A portion of this signal 22 may reflect back toward the ultrasound applicator 10 and the acoustic sensor 12. This acoustic response 22 may be detected by the acoustic sensor 12. The acoustic response 22 from the target tissue 20 prior to delivery of fluid may provide a baseline target tissue acoustic response that may be later compared with an acoustic response from the target tissue with the fluid delivered, as illustrated in FIG. 2B. FIG. 2B shows ultrasound applicator 10 broadcasting ultrasound 14 across the surface 16 of skin 18 of a patient toward a target tissue 20 and a delivered fluid 24 to disperse the delivered fluid into the target tissue 20. In response to the broadcasted ultrasound 14, the delivered fluid 24 may create an additional acoustic response signal. A portion of this signal 26 may be reflected back to sensor 12 and the target tissue 20 may reflect a signal 22 back toward the ultrasound applicator 10 and the acoustic sensor 12. The acoustic sensor 12 may detect signal 22 and signal 26 and may compare the acoustic response of the delivered fluid 24 and the target tissue 20 to the baseline acoustic response of the target tissue 20 (e.g., measured in FIG. 2A) to monitor a dispersal of the fluid 24. In some embodiments, an ultrasound delivery may be adjusted (e.g., terminated or the like) based on the fluid 24 dispersal monitoring. While the illustrated ultrasound applicator 10 includes an integrated acoustic sensor 12, it should be understood that the sensor 12 may be separate from the ultrasound applicator 10. When a separate acoustic and/or ultrasound sensor is used, a portion of the acoustic response of the tissue and/or injected fluid may be detected at a different location than the ultrasound delivery location. For example, the acoustic response detected may be in a forward direction relative to the acoustic applicator.

Temperature Safety Feature

As discussed above, the system 100 may include a temperature sensor for monitoring a temperature of a face of the ultrasound applicator 140. This may be an advantageous safety feature as the temperature sensor may provide temperature feedback to the system 100 and/or to the user indicating when the face of the ultrasound applicator 140 is above a safety threshold. In response to the measured temperature exceeding the safety threshold, the system 100 may adjust delivery of ultrasound and may also output a warning or alert to the user. Thus in some embodiments, a temperature safety monitoring method is provided.

Figure 3:
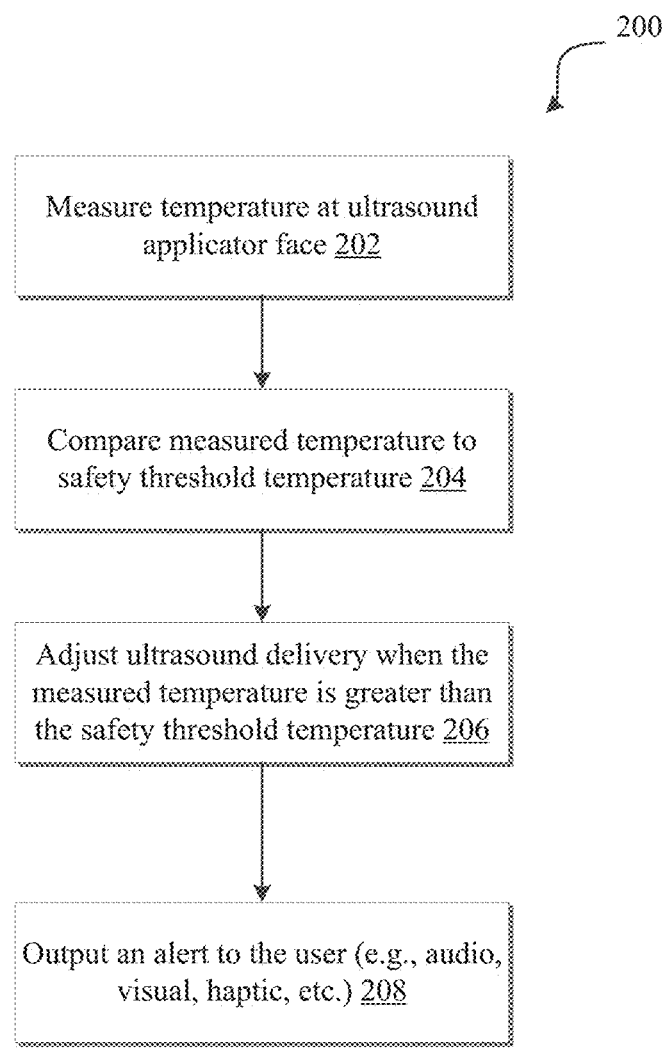
FIG. 3 illustrates an exemplary method of monitoring a temperature of an ultrasound applicator face according to some embodiments.

FIG. 3 illustrates an exemplary method 200 according to some embodiments of the present invention. At 202, a temperature of the ultrasound applicator face may be measured. At 204, the measured temperature may be compared to a safety threshold temperature. At 206, ultrasound delivery may be adjusted when the measured temperature is greater than the safety threshold temperature. At 208, an alert may be outputted to the user that is indicative of the adjustment in ultrasound delivery.

The temperature of the ultrasound applicator face may be measured by a separate temperature monitoring system. Alternatively, the temperature may be measured by an integrated temperature sensor. The sensor may be one or more of an infrared sensor, a thermocouple, thermistor, resistance temperature sensors, or the like or combinations thereof.

A temperature safety threshold may be preprogrammed into the system or may be set by a user. In some embodiments, multiple thresholds may be used. Each threshold may be associated with different adjustments to the ultrasound delivery and/or alerts to the user. For example, an intermediate threshold may be provided which is associated with an "intermediate caution" alert to the user. A higher threshold may also be used which is associated with an "extreme caution warning" alert to the user. In some embodiments, a safety threshold may be set between 42-46 degrees Celsius, preferably between 43-45 degrees Celsius, and even more preferably to about 44 degrees Celsius.

As set forth above, adjustments to the ultrasound delivery may be made when the measured temperature exceeds a set temperature threshold. For example, triggering an "extreme caution warning" may also be associated with a termination of the ultrasound delivery or a prevention of the application of ultrasound by the ultrasound applicator unit until the measured temperature of the ultrasound applicator falls below one or more of the thresholds. In some embodiments, the adjustment may be an adjustment of a power, frequency, or duration of ultrasound delivery. For example, in some embodiments, it may be preferable to decrease a power or frequency of ultrasound delivery when a temperature threshold is exceeded by a measured temperature. Such a decrease in power or frequency may allow the ultrasound dispersion to proceed for a longer duration as needed. In other embodiments, it may be desirable to immediately cease the delivery of ultrasound or to prevent the activation of the ultrasound transducer to prevent further heating and to reduce the chances of inadvertently injuring the patient when the measured temperature exceeds a safety threshold temperature.

An alert may be outputted by the system to the user. The alert may be indicative of an adjustment made to the ultrasound delivery. Optionally, the alert may be associated only with a measured temperature exceeding an intermediate threshold, where no adjustments to ultrasound delivery are made. The alert may be a visual alert, audio alert, and/or a haptic alert or combinations thereof. For example, the alert may be presented on a display of the system or output through one or more light sources (e.g., red, yellow, green LEDs or the like) on the ultrasound generator or the ultrasound applicator. Optionally, the alert may include a continuous sound or a one or a series of discrete beeps. An audio alert may be a record voice in some embodiments. For example, an audio warning from the system may advise the user to avoid contacting the applicator to the patient. Optionally, the alert may be a haptic vibration transmitted to the hand of the user of the system.

Thus, in some embodiments, it may be advantageous to include a temperature monitoring system to monitor a temperature of the ultrasound applicator face. This may reduce the possibility of inadvertent injury to a patient.

Ultrasound Duration Calculation

In some embodiments, it may be beneficial for a treatment system to be able to automatically calculate a duration for ultrasound application based on user inputted treatment parameters. This may provide an additional safety mechanism that reduces the possibility that a user applies ultrasound for too long a duration which may inadvertently injure a patient. Accordingly, in some embodiments, methods of calculating an ultrasound treatment duration are provided.

Figure 4:
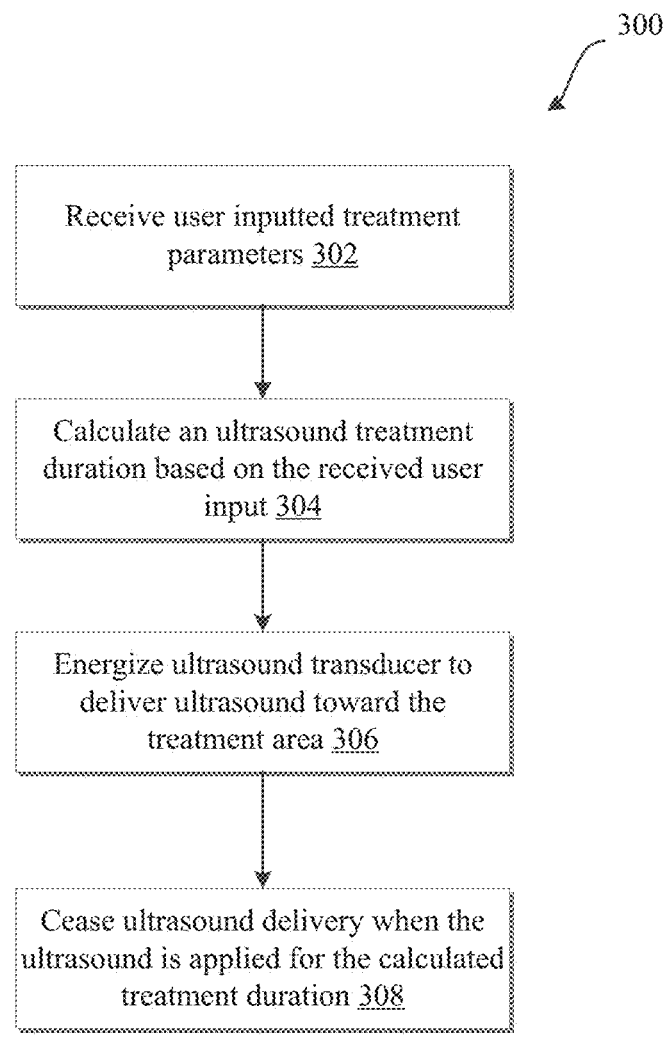
FIG. 4 illustrates an exemplary method of calculating ultrasound delivery duration according to some embodiments of the present invention.

FIG. 4 illustrates an exemplary method 300 according to some embodiments. At step 302, user inputted treatment parameters are received. At step 304, an ultrasound treatment duration is calculated based on the received user input. At step 306, the ultrasound transducer may be energized to deliver ultrasound toward the treatment area. At step 308, the ultrasound delivery may be terminated when the ultrasound is applied for the calculated treatment duration.

In some embodiments, a user interface may be provided with the treatment system. The user interface may allow a user to input parameters for the treatment such that the system may thereafter calculate a preferred duration for the ultrasound driven drug dispersion. For example, in some embodiments, a user interface may be provided for accepting a user inputted volume of fluid that is to be injected or infused into the patient. Based on the volume of fluid, the treatment system may calculate a duration for applying the ultrasound from the ultrasound applicator. In some embodiments, a treatment volume may be inputted by the user or parameters related to the treatment volume (e.g., treatment area and treatment depth). The system may then calculate the ultrasonic duration based on treatment volume. In some embodiments, the user may also input the desired power and frequency for the applied ultrasound and the calculated duration may be adjusted based on the inputted power and frequency. In some embodiments the ultrasound duration calculation may be performed using a preset power and frequency. Optionally, the system may calculate a range of durations with a range of powers and a range of frequencies. In some embodiments, the shortest duration out of the calculated ranges may be selected as an additional safety mechanism. In some embodiments, a diagnostic ultrasound component may be provided either separate or combined with the treatment applicator. The diagnostic ultrasound may be configured to map the depth of target tissue and the target tissue area, both before, during, and/or after injection of solution and during dispersion of the therapeutic agent. In some embodiments the treatment length and power output of the ultrasound dispersion applicator may be monitored by and adjusted in real time based upon the analysis of the tissue based upon the diagnostic ultrasonic array.

Thereafter, ultrasound may be applied toward the target tissue. The ultrasound may interact with a delivered fluid (e.g., via injection, infusion or the like) to disperse the fluid into the tissue of the patient. The system may monitor a duration of ultrasound delivery and may automatically cease the ultrasound delivery when the ultrasound has been delivered for the calculated duration.

Ultrasound Dispersal Monitoring

Figure 5:
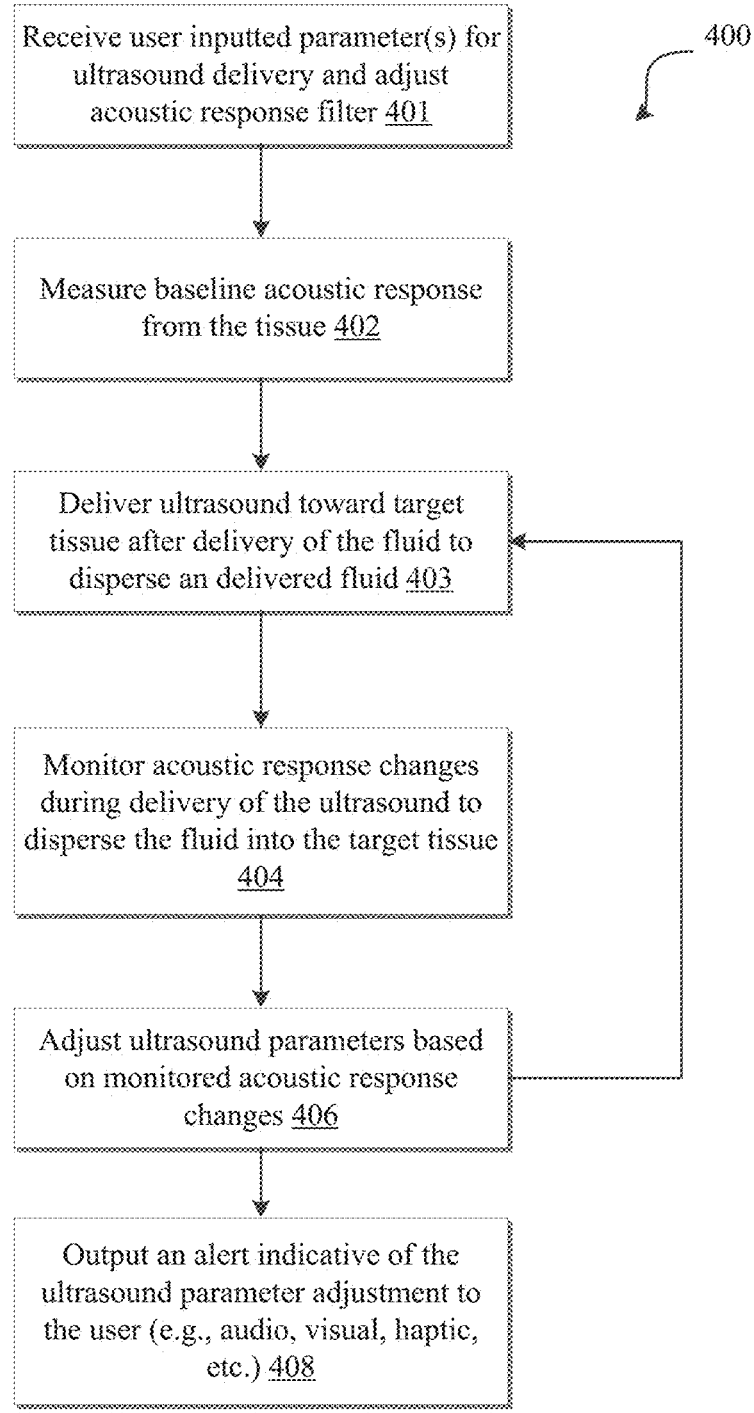
FIG. 5 illustrates an exemplary method of monitoring the progress of ultrasound drug dispersal according to some embodiments of the present invention.

In further embodiments, methods of monitoring ultrasound dispersal are provided. FIG. 5 illustrates an exemplary method 400 for monitoring dispersal of an agent into the target tissue using ultrasound. At step 401, one or more user inputted parameters may be received for ultrasound delivery and an acoustic response filter may be modified based on the one or more user inputted parameters. At step 402, a baseline acoustic response from the target tissue may be measured. At step 403, after delivery of the fluid, ultrasound may be delivered toward the target tissue to disperse the delivered fluid. At step 404, acoustic response changes may be monitored during the delivery of ultrasound to disperse the fluid into the target tissue. At step 406, adjustments to the ultrasound parameters may be made based on the monitored acoustic response changes. At step 408, an output to the user may be provided that is indicative of the adjustment to the ultrasound parameters.

Optionally, a user may input one or more parameters for ultrasound delivery 401 (e.g., power, frequency, etc.) as described above. When monitoring for baseline tissue acoustic responses and acoustic responses indicative of microstreaming and/or cavitation, it may be beneficial to include a signal filter. The signal filter may be configured to filter some frequencies from a return signal based on the user inputted parameters. In some embodiments, the sensor for monitoring an acoustic response may be configured to block frequencies returned that are equal to the inputted ultrasound frequencies. Put in another way, an acoustic response monitored may be the acoustic response at frequencies other than the inputted ultrasound frequency.

In some embodiments, the baseline acoustic response may be measured by an acoustic/ultrasonic sensor (e.g., piezoelectric transducer or the like) 402. A baseline acoustic response of the target tissue may be measured by delivering ultrasound toward the target tissue prior to delivery of the treatment fluid and measuring a reflected acoustic signal. In some embodiments, a harmonic response may be measured (e.g., second, third, fourth harmonic or sub-harmonics, or the like) and recorded. In some embodiments a broad band response may be measured and recorded. In some embodiments, it may be preferable if the ultrasound is delivered at a power and frequency that is used for subsequently dispersing the fluid into the tissue after fluid delivery. In some embodiments, the baseline target tissue acoustic response will have harmonics, but minimal sub harmonics and broad band responses.

After measuring the baseline acoustic response 402 from the target tissue and after fluid delivery into the tissue (e.g., via injection, infusion or the like) ultrasound may be applied to disperse the fluid into the target tissue 403. During ultrasound application toward the target tissue to disperse the fluid into the tissue, an acoustic response and changes in acoustic response may be monitored using the acoustic response sensor 404. In some embodiments, the acoustic response of the tissue is monitored. In some embodiments, the acoustic response of the fluid is monitored. In some embodiments, an acoustic response of an interaction between the solution and the tissue is monitored. In some embodiments, combinations of the acoustic response of the tissue, the fluid, and/or the interaction between the fluid with the tissue are monitored and recorded. Similar to the baseline acoustic response measurement, in some embodiments, a harmonic response may be monitored (e.g., second, third, fourth harmonic or sub-harmonics, or the like) during fluid dispersal. In some embodiments, a broad band response may be monitored during fluid dispersal. In some embodiments, the signal received is recorded at frequencies other than the applied frequency. For example, if a 1 MHz ultrasound is applied, the received of signal at frequencies other than 1 MHz is recorded. The ultrasound delivery may then be adjusted 406 based on changes in the recorded signal and/or by comparing the recorded signal to the baseline measurement.

According to some embodiments, changes in the acoustic response of the target tissue, the fluid, and/or an interaction between the fluid and the tissue during fluid dispersion into the tissue may be indicative of a need to adjust an ultrasound delivery parameter. By monitoring for these changes in acoustic response, a system may be configured to make automatic adjustments to the delivered ultrasound.

For example, in some embodiments, the power and frequency may be gradually increased until a desired strength of harmonic, subharmonic, and/or broad band response is achieved. A subharmonic at ½ the input frequency may be measured and may be indicative of dispersion through microstreaming and/or cavitation. In some embodiments higher harmonic strengths may be of interest (e.g., 2 f, 3 f, out to 10 f or the like) and measured by a spectrum analyzer. In some embodiments, broad band response may be associated with cavitation events within the fluid or microstreaming of the fluid into the interstitial space. In some embodiments, the injected fluid may generate a subharmonic response in response to the delivered ultrasound that is not typically generated by healthy tissue. Thus, a subharmonic response during delivery of the ultrasound may be associated with an amount of fluid that has not yet been dispersed. Accordingly, a subharmonic response during ultrasound delivery may be monitored and as the fluid is dispersed into the tissue, a subharmonic signal will go down. When the subharmonic signal disappears or returns to within a threshold of the baseline tissue response, ultrasound delivery may be ceased, according to some embodiments.

Optionally, in some embodiments, the monitored acoustic response may be compared to the measured baseline acoustic response. Adjustments to the ultrasound delivery may be based on a difference between the monitored acoustic response and the measured baseline acoustic response. In some embodiments when the monitored acoustic response during fluid dispersion returns to within a threshold of the measured baseline response, the system may adjust ultrasound delivery, for example by terminating the ultrasound delivery. In some embodiments, a spectral analyzer may be used to identify a difference or similarity between the monitored acoustic response and the baseline response. When the monitored acoustic response returns to within the threshold range of the measured baseline acoustic response, the fluid delivered to the patient may be sufficiently dispersed throughout the tissue.

Figure 6A:
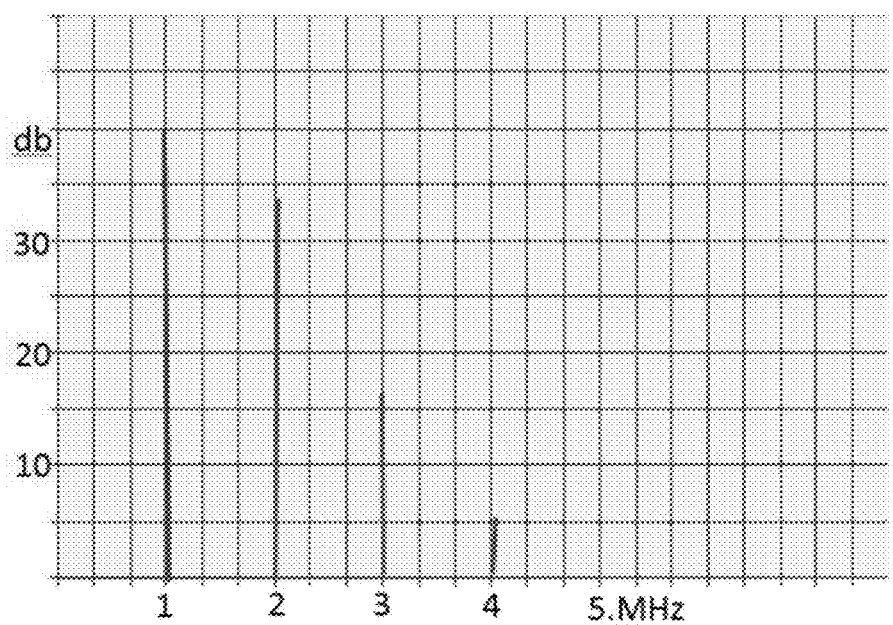
FIGS. 6A-6C illustrate an acoustic reaction of water under various conditions.
Figure 6B:
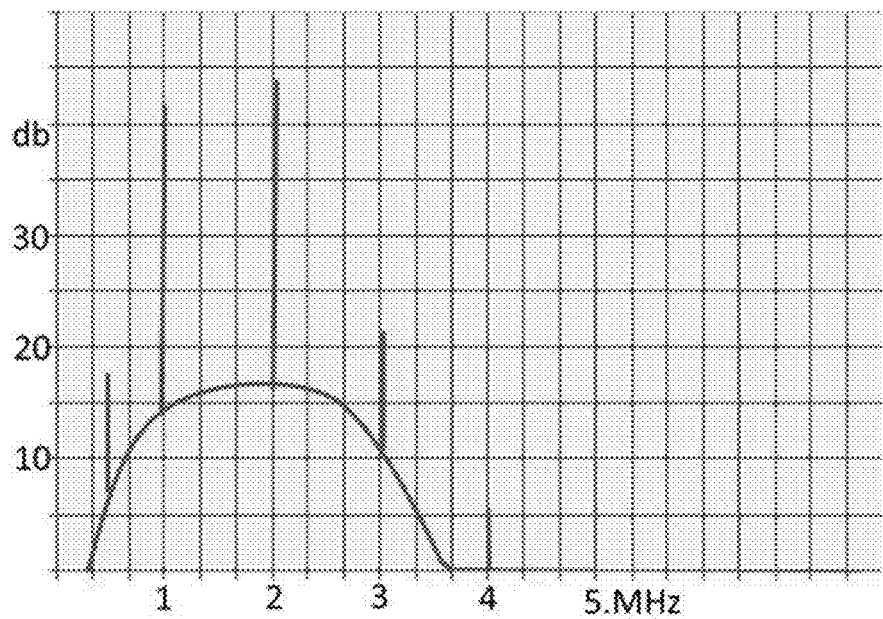
Figure 6C:
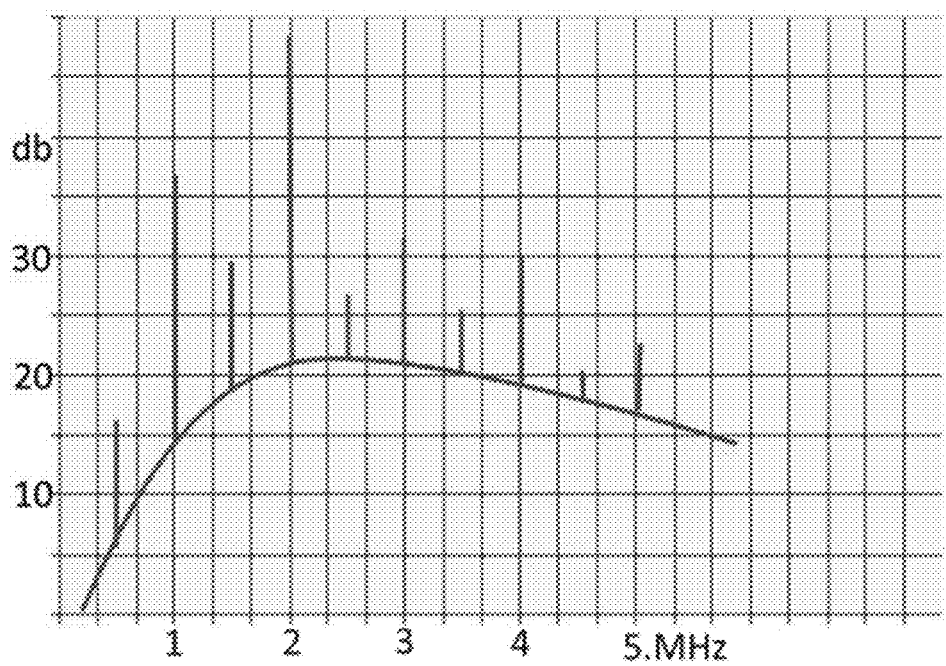

If dispersal is insufficient, adjustments to power and frequency of the applied ultrasound may be made. Additionally or alternatively, a partial pressure of gas in the injected fluid may be adjusted. In some embodiments, the partial pressure may be decreased such that a higher ultrasound level may be used. Optionally, the partial pressure may be increased to increase the amount of cavitation (and subharmonics and broad band response). Accordingly, in some embodiments, the injected fluid may act as an acoustic contrast agent due to the increase in gas content and induced cavitation. The gas content of the injected fluid may generate subharmonics not typically generated by tissue alone. Thus, as the fluid is dispersed into the tissue, a subharmonic signal will dissipate which will be indicative of a progress of the ultrasound drug dispersion procedure. For example, FIGS. 6A-6C show an exemplary acoustic response of water under low, medium, and higher acoustic powers (with signal noise suppressed). FIG. 6A shows an acoustic response of bulk water at low power—an input wave at about 1 MHz and higher harmonics at 2, 3 MHZ. The response which includes the input frequency and its harmonics may be representative of a baseline acoustic response from a tissue of a patient. Even at higher power levels such as to create an acoustic response illustrated FIG. 6B and FIG. 6C in bulk water, a patient's baseline tissue response (without infused or delivered fluid) will be qualitatively similar to the acoustic response shown in FIG. 6A, but may have different values of the peaks of the lines. FIG. 6B illustrates an acoustic response of bulk water with a power that is five times greater than in FIG. 6A. Here the acoustic response displaces cavitation in the broad band acoustic response and also strong subharmonics which is a response at (f/2, approximately 500 Hz). FIG. 6C illustrates an acoustic response of bulk water with a power that is five times greater than in FIG. 6B. Here, the subharmonic (f/2) and ultraharmonics (3 f/2, 5 f/2, etc.) are strong as is the broad band noise from internal cavitation. Various aspects of this spectrum with these features may be expected when the ultrasound is applied to a patient after fluid has been injected. The difference between the spectrum in FIG. 6C and the baseline spectrum acquired at the same acoustic power may be a measure of the progress of the ultrasonic drug dispersion. When dispersion is complete, the measured spectrum should return back toward the baseline which may have a form of the spectrum shown in FIG. 6A, but may have different values for the peaks. If the sound field power is not high enough, then the spectrum may be similar to that of FIG. 6A. Thus in some embodiments, traditional gas filled capsules as contrast agents are not used and thus acoustic responses (harmonic, subharmonic, or broad band responses) from gas filled capsules as contrast agents are not recorded and not used for monitoring drug dispersal through tissue.

Monitoring for dispersion of fluid and therapeutic agents may be particularly advantageous when treating cancerous tissue. Cancer tissue may have tighter interstitial spaces that are more difficult to penetrate with the injected fluid. Accordingly, monitoring an acoustic response of the target tissue, the injected fluid, and/or an interaction between the injected fluid and the target tissue may be advantageous for monitoring dispersion and making adjustments to ultrasound delivery when the fluid and therapeutic agent insufficiently disperse into the target tissue (e.g., cancer tissue, radiated tissue, or the like).

When the system adjusts ultrasound delivery, for example, by terminating the delivery of ultrasound, the system may output an alert according to some embodiments 408. The alert may be indicative of an adjustment made to the ultrasound delivery. The alert may be a visual alert, audio alert, and/or a haptic alert or combinations thereof. For example, the alert may be presented on a display of the system or output through one or more light sources (e.g., red, yellow, green LEDs or the like) on the ultrasound generator or the ultrasound applicator. Optionally, the alert may include a continuous sound or a one or a series of discrete beeps. An audio alert may be a record voice in some embodiments. For example, an audio alert from the system may advise the user that dispersion of the fluid and therapeutic agent is sufficient or complete. Optionally, the alert may be a haptic vibration transmitted to the hand of the user of the system.

Methods of Using Systems

According to some embodiments, methods of using the systems described above are provided. A subject can be in need of delivery of at least one therapeutic agent to at least one target tissue as described herein. In some embodiments, the target tissue can have a low blood supply. In some embodiments, the target tissue comprises tissue of an extremity, for example a leg, thing, knee, calf, foot, toe, arm, elbow, hand, finger, nose, ear, or the like. A system as described herein can be provided. In some embodiments, the system comprises a solution comprising the therapeutic agent in the container. In some embodiments, the operator prepares or places a solution comprising the therapeutic agent in the container. The operator can select a desired partial pressure of inert gas in the solution. In some embodiments, the operator applies a source of inert gas and/or a vacuum as described herein to increase or decrease the partial pressure to the desired level. In some embodiments, the solution is mixed or agitated as described herein to dissolve the inert gas in the solution. The operator can use the tissue interface of the system to apply the solution comprising a therapeutic agent to the target tissue directly, or to an area near the target tissue. The operator can then apply ultrasound energy to disperse the therapeutic agent in the target tissue. In some embodiments, the operator preselects a desired amount of cavitation, for example, so that a desired amount of dispersal in the target tissue can be achieved, thus achieving a desired concentration of therapeutic agent in the target tissue. In some embodiments, the system comprises a sensor, and automatically adjusts the ultrasound energy and/or frequency, and/or rate of administration of solution comprising therapeutic agent in order to maintain a desired level of cavitation. In some embodiments, therapeutic agent is administered for a specified period of time at the desired level of cavitation so as to achieve a desired concentration of therapeutic agent in the target tissue.

According to some embodiments, a method of delivering an antibiotic to an extremity of a subject is provided. The extremity can be otherwise untreatable by intravenous administration of antibiotic, for example due to low blood flow in the extremity. A system as described above can be provided. Inert gas can be applied to the solution while the solution is mixed or agitated, and/or a vacuum can be applied to the solution to arrive at a desired partial pressure of inert gas in the solution. The tissue interface of the system can be applied at or near the site of infection, and solution comprising the antibiotic can be administered. Ultrasound energy can be applied transcutaneously, using the ultrasound applicator of the system at or near the site of infection. An effective concentration of antibiotic can be delivered at or near the site of infection. In some embodiments, the sensor of the system detects acoustic feedback from the subject, and ultrasound parameters (for example power and/or frequency), and/or the rate of administration of fluid comprising the therapeutic agent are adjusted automatically so as to achieve a desired level of cavitation in fluid in the subject. In some embodiments, the extremity comprises a leg, thing, knee, calf, foot, toe, arm, elbow, hand, finger, nose, or ear. In some embodiments, the subject is diabetic. In some embodiments, the antibiotic comprises a beta-lactam antibiotic. In some embodiments, the antibiotic comprises Cefazolin. In some embodiments, the antibiotic comprises Vancomycin. In some embodiments, the antibiotic comprises Cefazolin, and the device comprises Cefazolin at a concentration of at least about 4000 µg/ml in solution. In some embodiments, upon dispersal in the target tissue, the Cefazolin is at a concentration of about 1000 µg/ml. In some embodiments, the system comprises a solution comprising the antibiotic agent in the container. In some embodiments, the operator prepares or places a solution comprising the therapeutic agent in the container. The operator can select a desired partial pressure of inert gas in the solution. In some embodiments, the operator applies a source of inert gas and/or a vacuum as described herein to increase or decrease the partial pressure to the desired level. In some embodiments, the solution is mixed or agitated as described herein to dissolve the inert gas in the solution.

EXAMPLE

An operator identifies a diabetic patient having an infection in a limb with limited blood flow at the site of infection. The operator prepares 100 cc of a saline solution comprising 1,000 µg/ml of Cefazolin and places it in the container of the system. The operator applies argon to the container while the system mixes the solution in the container, so as to achieve a partial pressure of argon of about 20 kPa. The operator administers a tissue interface comprising a cannula directly above the site of infection in the subject, and delivers the solution there. The operator uses the ultrasound applicator of the system to apply ultrasound energy at 100 kHz and 2 watts/cm$^2$ at the site of administration. Solution comprising Cefazolin is dispersed in the target tissue. In response to acoustic feedback from a sensor on the ultrasound applicator, the frequency and power of ultrasound energy are adjusted.

General

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. Headings are provided herein for organization purposes, and do not limit the scope of application of embodiments herein.

It will be understood by those skilled in the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

While the present invention has been described in some detail for purposes of clarity and understanding, one skilled in the art will appreciate that various changes in form and detail can be made without departing from the true scope of the invention.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

What is claimed is:

1. A method of monitoring a level of dispersal of a therapeutic agent into a target tissue, the method comprising:
    energizing an ultrasound transducer to deliver ultrasound energy toward a bolus of injected solution including the therapeutic agent dissolved therein to disperse the bolus of injected solution with the therapeutic agent into interstitial space of the target tissue;
    monitoring the level of dispersal of the bolus of injected solution with the therapeutic agent into the interstitial space of the target tissue, with an acoustic sensor in response to the ultrasound delivered by the ultrasound transducer, by monitoring an acoustic response of the target tissue or the injected solution to the applied ultrasound during an ultrasound application;
    adjusting the ultrasound delivery, with a controller coupled to the ultrasound transducer and the acoustic sensor, wherein adjusting is based on the monitored acoustic response of the target tissue or the injected solution to the applied ultrasound;
    measuring a baseline acoustic response from the target tissue, with the acoustic sensor, wherein the baseline acoustic response of the target tissue is associated with the acoustic response of the target tissue prior to injection of the solution; and
    identifying an end point for the ultrasound delivery, with the controller, by comparing the monitored acoustic response of the target tissue to the measured baseline acoustic response of the target tissue and ceasing the ultrasound delivery upon reaching the end point so as to facilitate delivery of ultrasound energy for a duration to disperse the injected solution within the target tissue while inhibiting tissue damage associated with prolonged ultrasound output, wherein comparing the monitored acoustic response of the target tissue to the measured baseline acoustic response of the target tissue comprises determining when the monitored acoustic response of the target tissue returns to within a predetermined threshold of the measured baseline acoustic response of the target tissue.

2. The method of claim 1, wherein monitoring the acoustic response of the target tissue or the injected solution comprises monitoring a harmonic, subharmonic, and/or broad band response of the target tissue or the injected solution to the applied ultrasound.

3. The method of claim 2, further comprising monitoring a harmonic, subharmonic, and/or broad band response of an interaction between the injected solution and the target tissue.

4. The method of claim 1, further comprising applying a Fast Fourier Transform to the monitored acoustic response of the target tissue or the injected solution to the applied ultrasound.

5. The method of claim 1, wherein the ultrasound transducer delivers ultrasound at an applied frequency and wherein monitoring the acoustic response of the target tissue comprises monitoring target tissue acoustic responses at frequencies other than the applied frequency.

6. The method of claim 5, wherein a second harmonic response from the target tissue or the injected solution is monitored.

* * * * *